(12) United States Patent
Sisken et al.

(10) Patent No.: US 9,364,277 B2
(45) Date of Patent: Jun. 14, 2016

(54) RF ENERGY CONTROLLER AND METHOD FOR ELECTROSURGICAL MEDICAL DEVICES

(71) Applicant: Cook Medical Technologies LLC, Bloomington, IN (US)

(72) Inventors: Richard B. Sisken, West Lafayette, IN (US); Jillian Faye Hrnicek, Arvada, CO (US); Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/651,889

(22) PCT Filed: Dec. 12, 2013

(86) PCT No.: PCT/US2013/074628
§ 371 (c)(1),
(2) Date: Jun. 12, 2015

(87) PCT Pub. No.: WO2014/093603
PCT Pub. Date: Jun. 19, 2014

(65) Prior Publication Data
US 2015/0313663 A1    Nov. 5, 2015

Related U.S. Application Data

(63) Continuation-in-part of application No. 13/713,648, filed on Dec. 13, 2012, now Pat. No. 9,204,921.

(51) Int. Cl.
*A61B 18/18*    (2006.01)
*A61B 18/12*    (2006.01)
*A61B 18/00*    (2006.01)

(52) U.S. Cl.
CPC ......... *A61B 18/1206* (2013.01); *A61B 18/1233* (2013.01); *A61B 2018/00577* (2013.01);
(Continued)

(58) Field of Classification Search
None
See application file for complete search history.

(56) References Cited

U.S. PATENT DOCUMENTS

| 4,231,372 A | 11/1980 | Newton |
| 4,301,801 A | 11/1981 | Schneiderman |

(Continued)

FOREIGN PATENT DOCUMENTS

| EP | 1 366 724 A1 | 12/2003 |
| WO | WO 93/20770 A2 | 10/1993 |

(Continued)

OTHER PUBLICATIONS

B.J. Dunkin et al., "Thin-layer ablation of human esophageal epithelium using a bipolar radiofrequency balloon device", Surgical Endoscopy (2006) 20; 125-130.

(Continued)

*Primary Examiner* — Kennedy Schaetzle
(74) *Attorney, Agent, or Firm* — Brinks Gilson & Lione

(57) ABSTRACT

A control unit controls delivery of RF energy generated by an RF generator to a medical device configured to perform a medical procedure. The control unit may be separate from the RF generator, and may have an input that may be attached to an output of the RF generator. The control unit includes switching circuitry that is closed while an amount of RF energy is transmitted through the control unit to the medical device. The switching circuitry opens when the amount of RF energy reaches a threshold level.

20 Claims, 17 Drawing Sheets

(52) U.S. Cl.
CPC .......... *A61B2018/00589* (2013.01); *A61B 2018/00642* (2013.01); *A61B 2018/00648* (2013.01); *A61B 2018/00678* (2013.01); *A61B 2018/00702* (2013.01); *A61B 2018/00708* (2013.01); *A61B 2018/00779* (2013.01); *A61B 2018/00827* (2013.01); *A61B 2018/00886* (2013.01); *A61B 2018/00892* (2013.01); *A61B 2018/00898* (2013.01); *A61B 2018/00988* (2013.01); *A61B 2018/124* (2013.01)

(56) References Cited

U.S. PATENT DOCUMENTS

| | | |
|---|---|---|
| 4,532,924 A | 8/1985 | Auth et al. |
| 4,651,280 A | 3/1987 | Chang et al. |
| 4,765,331 A | 8/1988 | Petruzzi et al. |
| 4,860,745 A | 8/1989 | Farin et al. |
| 4,898,169 A | 2/1990 | Norman et al. |
| 4,898,179 A | 2/1990 | Sirota |
| 4,959,710 A | 9/1990 | Uehara et al. |
| 5,162,725 A | 11/1992 | Hodson et al. |
| 5,244,462 A | 9/1993 | Delahuerga et al. |
| 5,350,376 A | 9/1994 | Brown |
| 5,383,874 A | 1/1995 | Jackson et al. |
| 5,400,267 A | 3/1995 | Denen et al. |
| 5,423,809 A | 6/1995 | Klicek |
| 5,425,375 A | 6/1995 | Chin et al. |
| 5,437,664 A | 8/1995 | Cohen et al. |
| 5,484,400 A | 1/1996 | Edwards et al. |
| 5,505,730 A | 4/1996 | Edwards |
| 5,520,684 A | 5/1996 | Imran |
| 5,558,619 A | 9/1996 | Kami et al. |
| 5,558,672 A | 9/1996 | Edwards et al. |
| 5,569,241 A | 10/1996 | Edwards |
| 5,575,788 A | 11/1996 | Baker et al. |
| 5,665,062 A | 9/1997 | Houser |
| 5,669,876 A | 9/1997 | Schechter et al. |
| 5,681,308 A | 10/1997 | Edwards et al. |
| 5,713,942 A | 2/1998 | Stern et al. |
| 5,735,847 A | 4/1998 | Gough et al. |
| 5,746,224 A | 5/1998 | Edwards |
| 5,769,846 A | 6/1998 | Edwards et al. |
| 5,800,429 A | 9/1998 | Edwards |
| 5,817,091 A | 10/1998 | Nardella et al. |
| 5,823,197 A | 10/1998 | Edwards |
| 5,827,273 A | 10/1998 | Edwards |
| 5,827,277 A | 10/1998 | Edwards |
| 5,843,020 A | 12/1998 | Tu et al. |
| 5,843,075 A | 12/1998 | Taylor |
| 5,843,077 A | 12/1998 | Edwards |
| 5,843,152 A | 12/1998 | Tu et al. |
| 5,846,236 A | 12/1998 | Lindenmeier et al. |
| 5,849,010 A | 12/1998 | Wurzer et al. |
| 5,868,737 A | 2/1999 | Taylor et al. |
| 5,871,481 A | 2/1999 | Kannenberg et al. |
| 5,876,369 A | 3/1999 | Houser |
| 5,897,553 A | 4/1999 | Mulier et al. |
| 5,899,917 A | 5/1999 | Edwards et al. |
| 5,902,328 A | 5/1999 | LaFontaine et al. |
| 5,913,856 A | 6/1999 | Chia et al. |
| 5,925,038 A | 7/1999 | Panescu et al. |
| 5,944,715 A | 8/1999 | Goble et al. |
| 5,948,009 A | 9/1999 | Tu |
| 5,954,649 A | 9/1999 | Chia et al. |
| 5,954,717 A | 9/1999 | Behl et al. |
| 5,957,920 A | 9/1999 | Baker |
| 5,957,922 A | 9/1999 | Imran |
| 5,964,727 A | 10/1999 | Edwards et al. |
| 5,964,755 A | 10/1999 | Edwards |
| 5,971,980 A | 10/1999 | Sherman |
| 5,980,517 A | 11/1999 | Gough |
| 5,991,355 A | 11/1999 | Dahlke |
| 6,002,968 A | 12/1999 | Edwards |
| 6,004,319 A | 12/1999 | Goble et al. |
| 6,006,755 A | 12/1999 | Edwards |
| 6,009,877 A | 1/2000 | Edwards |
| 6,013,074 A | 1/2000 | Taylor |
| 6,013,076 A | 1/2000 | Goble et al. |
| 6,015,406 A | 1/2000 | Goble et al. |
| 6,022,346 A | 2/2000 | Panescu et al. |
| 6,024,743 A | 2/2000 | Edwards |
| 6,027,501 A | 2/2000 | Goble et al. |
| 6,033,401 A | 3/2000 | Edwards et al. |
| 6,039,757 A | 3/2000 | Edwards et al. |
| 6,041,260 A | 3/2000 | Stern et al. |
| 6,044,846 A | 4/2000 | Edwards |
| 6,056,744 A | 5/2000 | Edwards |
| 6,056,745 A | 5/2000 | Panescu et al. |
| 6,056,746 A | 5/2000 | Goble et al. |
| 6,056,747 A | 5/2000 | Saadat et al. |
| 6,059,778 A | 5/2000 | Sherman |
| 6,063,081 A | 5/2000 | Mulier et al. |
| 6,066,139 A | 5/2000 | Ryan et al. |
| 6,068,653 A | 5/2000 | LaFontaine |
| 6,080,150 A | 6/2000 | Gough |
| 6,083,223 A | 7/2000 | Baker |
| 6,090,106 A | 7/2000 | Goble et al. |
| 6,092,528 A | 7/2000 | Edwards et al. |
| 6,093,186 A | 7/2000 | Goble |
| 6,113,592 A | 9/2000 | Taylor |
| 6,113,596 A | 9/2000 | Hooven et al. |
| 6,123,702 A | 9/2000 | Swanson et al. |
| 6,132,425 A | 10/2000 | Gough |
| 6,139,569 A | 10/2000 | Ingle et al. |
| 6,156,060 A | 12/2000 | Roy et al. |
| 6,165,206 A | 12/2000 | Tu |
| 6,168,594 B1 | 1/2001 | LaFontaine et al. |
| 6,174,308 B1 | 1/2001 | Goble et al. |
| 6,179,833 B1 | 1/2001 | Taylor |
| 6,183,468 B1 | 2/2001 | Swanson et al. |
| 6,190,382 B1 | 2/2001 | Ormsby et al. |
| 6,200,314 B1 | 3/2001 | Sherman |
| 6,217,576 B1 | 4/2001 | Tu et al. |
| 6,226,554 B1 | 5/2001 | Tu et al. |
| 6,233,477 B1 | 5/2001 | Chia et al. |
| 6,235,022 B1 | 5/2001 | Hallock et al. |
| 6,235,023 B1 | 5/2001 | Lee et al. |
| 6,236,891 B1 | 5/2001 | Ingle et al. |
| 6,237,604 B1 | 5/2001 | Burnside et al. |
| 6,245,065 B1 | 6/2001 | Panescu et al. |
| 6,245,067 B1 | 6/2001 | Tu et al. |
| 6,246,899 B1 | 6/2001 | Chia et al. |
| 6,254,598 B1 | 7/2001 | Edwards et al. |
| 6,258,087 B1 | 7/2001 | Edwards et al. |
| 6,259,941 B1 | 7/2001 | Chia et al. |
| 6,264,653 B1 | 7/2001 | Falwell |
| 6,266,551 B1 | 7/2001 | Osadchy et al. |
| 6,273,886 B1 | 8/2001 | Edwards et al. |
| 6,280,441 B1 | 8/2001 | Ryan |
| 6,287,303 B1 | 9/2001 | Geistert et al. |
| 6,293,942 B1 | 9/2001 | Goble et al. |
| 6,293,943 B1 | 9/2001 | Panescu et al. |
| 6,315,776 B1 | 11/2001 | Edwards |
| 6,322,558 B1 | 11/2001 | Taylor et al. |
| 6,322,584 B2 | 11/2001 | Ingle et al. |
| 6,325,798 B1 | 12/2001 | Edwards et al. |
| 6,346,104 B2 | 2/2002 | Daly et al. |
| 6,355,031 B1 | 3/2002 | Edwards et al. |
| 6,358,245 B1 | 3/2002 | Edwards et al. |
| 6,387,092 B1 | 5/2002 | Burnside et al. |
| 6,398,779 B1 | 6/2002 | Buysse et al. |
| 6,402,744 B2 | 6/2002 | Edwards et al. |
| 6,405,732 B1 | 6/2002 | Edwards et al. |
| 6,409,722 B1 | 6/2002 | Hoey et al. |
| 6,440,128 B1 | 8/2002 | Edwards et al. |
| 6,464,689 B1 | 10/2002 | Qin et al. |
| 6,464,697 B1 | 10/2002 | Edwards et al. |
| 6,468,204 B2 | 10/2002 | Sendai et al. |
| 6,475,216 B2 | 11/2002 | Mulier et al. |
| 6,488,678 B2 | 12/2002 | Sherman |
| 6,508,815 B1 | 1/2003 | Strul et al. |
| 6,517,535 B2 | 2/2003 | Edwards |
| 6,533,778 B2 | 3/2003 | Herzon |
| 6,535,768 B1 | 3/2003 | Baker et al. |

(56) References Cited

U.S. PATENT DOCUMENTS

| | | | |
|---|---|---|---|
| 6,537,272 B2 | 3/2003 | Christopherson et al. |
| 6,551,310 B1 | 4/2003 | Ganz et al. |
| 6,562,034 B2 | 5/2003 | Edwards et al. |
| 6,587,750 B2 | 7/2003 | Gerbi et al. |
| 6,620,157 B1 | 9/2003 | Dabney et al. |
| 6,629,974 B2 | 10/2003 | Penny et al. |
| 6,641,580 B1 | 11/2003 | Edwards et al. |
| 6,645,201 B1 | 11/2003 | Utley et al. |
| 6,651,669 B1 | 11/2003 | Burnside |
| 6,652,514 B2 | 11/2003 | Ellman et al. |
| 6,660,002 B1 | 12/2003 | Edwards et al. |
| 6,663,625 B1 | 12/2003 | Ormsby et al. |
| 6,673,070 B2 | 1/2004 | Edwards et al. |
| 6,676,660 B2 | 1/2004 | Wampler |
| 6,682,527 B2 | 1/2004 | Strul |
| 6,685,700 B2 | 2/2004 | Behl et al. |
| 6,689,127 B1 | 2/2004 | Gough et al. |
| 6,692,490 B1 | 2/2004 | Edwards |
| 6,712,074 B2 | 3/2004 | Edwards et al. |
| 6,712,814 B2 | 3/2004 | Edwards et al. |
| 6,723,091 B2 | 4/2004 | Goble et al. |
| 6,723,092 B2 | 4/2004 | Brown et al. |
| 6,730,077 B2 | 5/2004 | Carroll et al. |
| 6,730,079 B2 | 5/2004 | Lovewell |
| 6,733,495 B1 | 5/2004 | Bek et al. |
| 6,736,810 B2 | 5/2004 | Hoey et al. |
| 6,740,082 B2 | 5/2004 | Shadduck |
| 6,783,523 B2 | 8/2004 | Qin et al. |
| 6,790,206 B2 | 9/2004 | Panescu |
| 6,790,207 B2 | 9/2004 | Utley et al. |
| 6,796,981 B2 | 9/2004 | Wham et al. |
| 6,802,841 B2 | 10/2004 | Utley et al. |
| 6,805,128 B1 | 10/2004 | Pless et al. |
| 6,808,525 B2 | 10/2004 | Latterell et al. |
| 6,827,713 B2 | 12/2004 | Bek et al. |
| 6,827,715 B2 | 12/2004 | Francischelli et al. |
| 6,855,141 B2 | 2/2005 | Lovewell |
| 6,872,206 B2 | 3/2005 | Edwards et al. |
| 6,923,805 B1 | 8/2005 | La Fontaine et al. |
| 6,929,641 B2 | 8/2005 | Goble et al. |
| 6,936,024 B1 | 8/2005 | Houser |
| 6,966,907 B2 | 11/2005 | Goble et al. |
| 6,974,456 B2 | 12/2005 | Edwards et al. |
| 6,984,231 B2 | 1/2006 | Goble et al. |
| 6,994,704 B2 | 2/2006 | Qin et al. |
| 7,004,938 B2 | 2/2006 | Ormsby et al. |
| 7,008,421 B2 | 3/2006 | Daniel et al. |
| 7,041,096 B2 | 5/2006 | Malis et al. |
| 7,048,687 B1 | 5/2006 | Reuss et al. |
| 7,056,320 B2 | 6/2006 | Utley et al. |
| 7,070,595 B2 | 7/2006 | Ormsby et al. |
| 7,122,031 B2 | 10/2006 | Edwards et al. |
| 7,125,407 B2 | 10/2006 | Edwards et al. |
| 7,137,980 B2 | 11/2006 | Buysse et al. |
| 7,150,745 B2 | 12/2006 | Stern et al. |
| 7,165,551 B2 | 1/2007 | Edwards et al. |
| 7,195,627 B2 | 3/2007 | Amoah et al. |
| 7,211,081 B2 | 5/2007 | Goble |
| 7,214,224 B2 | 5/2007 | Goble |
| 7,223,264 B2 | 5/2007 | Daniel et al. |
| 7,250,050 B2 | 7/2007 | Ryan |
| 7,258,688 B1 | 8/2007 | Shah et al. |
| 7,278,991 B2 | 10/2007 | Morris et al. |
| 7,282,048 B2 | 10/2007 | Goble et al. |
| 7,282,049 B2 | 10/2007 | Orszulak et al. |
| 7,293,563 B2 | 11/2007 | Utley et al. |
| 7,300,436 B2 | 11/2007 | Penny et al. |
| 7,300,437 B2 | 11/2007 | Pozzato |
| 7,303,557 B2 | 12/2007 | Wham et al. |
| 7,329,254 B2 | 2/2008 | West et al. |
| 7,335,199 B2 | 2/2008 | Goble et al. |
| 7,341,586 B2 | 3/2008 | Daniel et al. |
| 7,344,532 B2 | 3/2008 | Goble et al. |
| 7,344,535 B2 | 3/2008 | Stern et al. |
| 7,353,068 B2 | 4/2008 | Tanaka et al. |
| 7,364,577 B2 | 4/2008 | Wham et al. |
| 7,367,974 B2 | 5/2008 | Haemmerich et al. |
| 7,422,586 B2 | 9/2008 | Morris et al. |
| 7,458,378 B2 | 12/2008 | Utley et al. |
| 7,465,301 B2 | 12/2008 | Bek et al. |
| 7,468,060 B2 | 12/2008 | Utley et al. |
| 7,507,234 B2 | 3/2009 | Utley et al. |
| 7,507,238 B2 | 3/2009 | Edwards et al. |
| 7,520,877 B2 | 4/2009 | Lee, Jr. et al. |
| 7,530,979 B2 | 5/2009 | Ganz et al. |
| 7,553,309 B2 | 6/2009 | Buysse et al. |
| 7,556,628 B2 | 7/2009 | Utley et al. |
| 7,571,003 B2 | 8/2009 | Pozzato |
| 7,585,296 B2 | 9/2009 | Edwards et al. |
| 7,594,913 B2 | 9/2009 | Ormsby et al. |
| 7,630,774 B2 | 12/2009 | Karni et al. |
| 7,632,268 B2 | 12/2009 | Edwards et al. |
| 7,648,500 B2 | 1/2010 | Edwards et al. |
| 7,674,260 B2 | 3/2010 | Sampson et al. |
| 7,689,292 B2 | 3/2010 | Hadzic et al. |
| 7,699,842 B2 | 4/2010 | Buysse et al. |
| 7,699,844 B2 | 4/2010 | Utley et al. |
| 7,713,267 B2 | 5/2010 | Pozzato |
| 7,780,662 B2 | 8/2010 | Bahney |
| 7,785,322 B2 | 8/2010 | Penny et al. |
| 7,803,156 B2 | 9/2010 | Eder et al. |
| 7,862,564 B2 | 1/2011 | Goble |
| 7,862,565 B2 | 1/2011 | Eder et al. |
| 7,879,032 B1 | 2/2011 | Garito et al. |
| 7,883,508 B2 | 2/2011 | Thao et al. |
| 7,901,400 B2 | 3/2011 | Wham et al. |
| 7,922,715 B2 | 4/2011 | Qin et al. |
| 7,942,874 B2 | 5/2011 | Eder et al. |
| 7,955,326 B2 | 6/2011 | Paul et al. |
| 7,959,627 B2 | 6/2011 | Utley et al. |
| 7,972,328 B2 | 7/2011 | Wham et al. |
| 7,976,540 B2 | 7/2011 | Daw et al. |
| 7,993,332 B2 | 8/2011 | Goble et al. |
| 7,993,336 B2 | 8/2011 | Jackson et al. |
| 7,993,338 B2 | 8/2011 | Klimovitch et al. |
| 7,997,278 B2 | 8/2011 | Utley et al. |
| 8,002,769 B2 | 8/2011 | Goble et al. |
| 8,012,149 B2 | 9/2011 | Jackson et al. |
| 8,062,290 B2 | 11/2011 | Buysse et al. |
| 8,100,133 B2 | 1/2012 | Mintz et al. |
| 8,104,956 B2 | 1/2012 | Blaha |
| 8,133,222 B2 | 3/2012 | Ormsby |
| 8,147,485 B2 | 4/2012 | Wham et al. |
| 8,152,801 B2 | 4/2012 | Goldberg et al. |
| 8,152,803 B2 | 4/2012 | Edwards et al. |
| 8,192,426 B2 | 6/2012 | Stern et al. |
| 8,197,476 B2 | 6/2012 | Truckai |
| 8,197,477 B2 | 6/2012 | Truckai |
| 8,206,381 B2 | 6/2012 | Lischinsky et al. |
| 8,216,223 B2 | 7/2012 | Wham et al. |
| 8,251,992 B2 | 8/2012 | Utley et al. |
| 8,257,346 B2 | 9/2012 | Qin et al. |
| 8,273,012 B2 | 9/2012 | Wallace et al. |
| 8,277,495 B2 | 10/2012 | Demetriou et al. |
| 8,298,226 B2 | 10/2012 | Hosier |
| 8,303,583 B2 | 11/2012 | Hosier et al. |
| 8,308,722 B2 | 11/2012 | Ormsby et al. |
| 8,348,948 B2 | 1/2013 | Bahney |
| 8,372,067 B2 | 2/2013 | Woloszko et al. |
| 8,398,626 B2 | 3/2013 | Buysse et al. |
| 8,398,627 B2 | 3/2013 | Hosier |
| 8,409,174 B2 | 4/2013 | Omori |
| 8,409,192 B2 | 4/2013 | Asirvatham et al. |
| 8,439,908 B2 | 5/2013 | Utley et al. |
| 8,452,383 B2 | 5/2013 | Norris et al. |
| 8,486,065 B2 | 7/2013 | Lee et al. |
| 8,568,405 B2 | 10/2013 | Cox et al. |
| 8,574,229 B2 | 11/2013 | Eder et al. |
| 8,597,287 B2 | 12/2013 | Benamou et al. |
| 8,613,743 B2 | 12/2013 | Selig |
| 8,636,736 B2 | 1/2014 | Yates et al. |
| 8,641,704 B2 | 2/2014 | Werneth et al. |
| 8,641,711 B2 | 2/2014 | Kelly et al. |
| 8,646,460 B2 | 2/2014 | Utley et al. |

(56) References Cited

U.S. PATENT DOCUMENTS

| | | |
|---|---|---|
| 8,657,817 B2 | 2/2014 | Fischer et al. |
| 8,672,934 B2 | 3/2014 | Benamou et al. |
| 8,685,016 B2 | 4/2014 | Wham et al. |
| 8,685,018 B2 | 4/2014 | Cox et al. |
| 8,696,662 B2 | 4/2014 | Eder et al. |
| 8,702,690 B2 | 4/2014 | Paul et al. |
| 8,702,694 B2 | 4/2014 | Wallace et al. |
| 8,728,072 B2 | 5/2014 | Eder et al. |
| 8,747,401 B2 | 6/2014 | Gonzalez et al. |
| 8,771,269 B2 | 7/2014 | Sherman et al. |
| 8,777,877 B2 | 7/2014 | Stein et al. |
| 8,784,338 B2 | 7/2014 | Wallace et al. |
| 8,821,486 B2 | 9/2014 | Toth et al. |
| 8,822,875 B2 | 9/2014 | Webster et al. |
| 8,838,206 B2 | 9/2014 | Mohajer |
| 8,840,588 B2 | 9/2014 | Clement et al. |
| 8,876,816 B2 | 11/2014 | Hosier |
| 8,920,414 B2 | 12/2014 | Stone et al. |
| 8,932,285 B2 | 1/2015 | Morris et al. |
| 8,939,970 B2 | 1/2015 | Stone et al. |
| 8,961,506 B2 | 2/2015 | McCarthy et al. |
| 8,968,296 B2 | 3/2015 | McPherson |
| 8,979,838 B2 | 3/2015 | Woloszko et al. |
| 2003/0204185 A1 | 10/2003 | Sherman et al. |
| 2004/0087936 A1 | 5/2004 | Stern et al. |
| 2004/0215235 A1 | 10/2004 | Jackson et al. |
| 2004/0215296 A1 | 10/2004 | Ganz et al. |
| 2005/0096644 A1 | 5/2005 | Hall et al. |
| 2006/0079883 A1 | 4/2006 | Elmouelhi et al. |
| 2006/0224151 A1 | 10/2006 | Waaler |
| 2006/0235378 A1 | 10/2006 | Waaler |
| 2008/0015563 A1 | 1/2008 | Hoey et al. |
| 2008/0091195 A1 | 4/2008 | Sliwa et al. |
| 2008/0097422 A1 | 4/2008 | Edwards et al. |
| 2008/0103498 A1 | 5/2008 | West et al. |
| 2008/0172052 A1 | 7/2008 | Eder et al. |
| 2009/0012518 A1 | 1/2009 | Utley et al. |
| 2009/0036882 A1 | 2/2009 | Webster et al. |
| 2009/0048593 A1 | 2/2009 | Ganz et al. |
| 2009/0054889 A1 | 2/2009 | Newton et al. |
| 2009/0093805 A1 | 4/2009 | Bek et al. |
| 2009/0118699 A1 | 5/2009 | Utley et al. |
| 2009/0182321 A1 | 7/2009 | McGreevy et al. |
| 2009/0248019 A1 | 10/2009 | Falkenstein et al. |
| 2009/0254079 A1 | 10/2009 | Edwards et al. |
| 2009/0318914 A1 | 12/2009 | Utley et al. |
| 2010/0004648 A1 | 1/2010 | Edwards et al. |
| 2010/0042093 A9 | 2/2010 | Wham et al. |
| 2010/0057071 A1 | 3/2010 | Amoah et al. |
| 2010/0069942 A1 | 3/2010 | Shelton, IV |
| 2010/0087809 A1 | 4/2010 | Edwards et al. |
| 2010/0114087 A1 | 5/2010 | Edwards et al. |
| 2010/0121320 A1 | 5/2010 | Hosier et al. |
| 2010/0204694 A1 | 8/2010 | Mehta et al. |
| 2010/0274239 A1 | 10/2010 | Paul et al. |
| 2010/0331833 A1 | 12/2010 | Maschke et al. |
| 2011/0022041 A1 | 1/2011 | Ingle et al. |
| 2011/0071468 A1 | 3/2011 | Utley et al. |
| 2011/0087212 A1 | 4/2011 | Aldridge et al. |
| 2011/0098698 A1 | 4/2011 | Bek et al. |
| 2011/0112529 A1 | 5/2011 | Shikhman |
| 2011/0125146 A1 | 5/2011 | Greeley et al. |
| 2011/0172659 A1 | 7/2011 | Brannan |
| 2011/0178515 A1 | 7/2011 | Bloom et al. |
| 2011/0184404 A1 | 7/2011 | Walberg et al. |
| 2011/0190759 A1 | 8/2011 | Qin et al. |
| 2011/0202050 A1 | 8/2011 | Brewer et al. |
| 2011/0306960 A1 | 12/2011 | Eisele et al. |
| 2012/0004645 A1 | 1/2012 | Dastani |
| 2012/0004656 A1 | 1/2012 | Jackson et al. |
| 2012/0116156 A1 | 5/2012 | Lederman |
| 2012/0143177 A1 | 6/2012 | Avitall |
| 2012/0157838 A1 | 6/2012 | Adanny et al. |
| 2012/0157986 A1 | 6/2012 | Stone et al. |
| 2012/0158101 A1 | 6/2012 | Stone et al. |
| 2012/0165807 A1 | 6/2012 | Daw et al. |
| 2012/0203219 A1 | 8/2012 | Evans et al. |
| 2012/0209288 A1 | 8/2012 | Robinson |
| 2012/0239025 A1 | 9/2012 | Smith |
| 2012/0239028 A1 | 9/2012 | Wallace et al. |
| 2012/0283731 A1 | 11/2012 | Unger et al. |
| 2012/0283732 A1 | 11/2012 | Lam |
| 2012/0310311 A1 | 12/2012 | Elkah |
| 2013/0117669 A1 | 5/2013 | Shikhman et al. |
| 2013/0158634 A1 | 6/2013 | Ron Edoute et al. |
| 2013/0165916 A1 | 6/2013 | Mathur et al. |
| 2013/0165917 A1 | 6/2013 | Mathur et al. |
| 2013/0165918 A1 | 6/2013 | Riff |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0184701 A1 | 7/2013 | Dunning |
| 2013/0197503 A1 | 8/2013 | Orszulak |
| 2013/0197506 A1 | 8/2013 | Evans et al. |
| 2013/0197508 A1 | 8/2013 | Shikhman et al. |
| 2013/0211398 A1 | 8/2013 | Daw et al. |
| 2013/0226173 A1 | 8/2013 | Utley et al. |
| 2013/0231611 A1 | 9/2013 | Lischinsky et al. |
| 2013/0237979 A1 | 9/2013 | Shikhman et al. |
| 2013/0238062 A1 | 9/2013 | Ron Edoute et al. |
| 2013/0261613 A1 | 10/2013 | Norris et al. |
| 2013/0267943 A1 | 10/2013 | Hancock |
| 2013/0282085 A1 | 10/2013 | Lischinsky et al. |
| 2013/0304061 A1 | 11/2013 | Chang et al. |
| 2013/0317494 A1 | 11/2013 | Daw et al. |
| 2013/0345689 A1 | 12/2013 | Ruddenklau et al. |
| 2014/0018798 A1 | 1/2014 | Cox et al. |
| 2014/0025061 A1 | 1/2014 | Benamou |
| 2014/0058374 A1 | 2/2014 | Edmunds et al. |
| 2014/0058382 A1 | 2/2014 | Yang |
| 2014/0073858 A1 | 3/2014 | Sherwinter |
| 2014/0074090 A1 | 3/2014 | Lam et al. |
| 2014/0148802 A1 | 5/2014 | LeMay |
| 2014/0155882 A1 | 6/2014 | Cox et al. |
| 2014/0163359 A1 | 6/2014 | Sholev et al. |
| 2014/0163549 A1 | 6/2014 | Yates et al. |
| 2014/0207217 A1 | 7/2014 | Lischinsky et al. |
| 2014/0236139 A1 | 8/2014 | Payman |
| 2014/0238175 A1 | 8/2014 | Huszar et al. |
| 2014/0238176 A1 | 8/2014 | Huszar et al. |
| 2014/0276749 A1 | 9/2014 | Johnson |
| 2014/0276753 A1 | 9/2014 | Wham et al. |
| 2014/0276754 A1 | 9/2014 | Gilbert et al. |
| 2014/0288546 A1 | 9/2014 | Sherman et al. |
| 2014/0296629 A1 | 10/2014 | Chang et al. |
| 2014/0296846 A1 | 10/2014 | Huszar et al. |
| 2014/0296848 A1 | 10/2014 | Chang et al. |
| 2014/0296902 A1 | 10/2014 | Huszar et al. |
| 2014/0330353 A1 | 11/2014 | Knight |
| 2014/0336632 A1 | 11/2014 | Toth et al. |
| 2014/0336636 A1 | 11/2014 | Huszar et al. |
| 2014/0350564 A1 | 11/2014 | Huszar et al. |
| 2015/0032094 A1 | 1/2015 | Kane et al. |
| 2015/0032100 A1 | 1/2015 | Coulson et al. |

FOREIGN PATENT DOCUMENTS

| | | | |
|---|---|---|---|
| WO | WO 95/09577 A1 | 4/1995 | |
| WO | WO 2006/017666 A2 | 2/2006 | |

OTHER PUBLICATIONS

R.M. Bremner et al, "Ultrasonic epithelial ablation of the lower esophagus without stricture formation", Surgical Endoscopy (1998) 12; 342-347.

C.P. Barham et al., "Photothermal laser ablation of Barrett's oesophagus: endoscopic and histological evidence of squamous re-epithelialisation", Gut (1997); 41: 281-284.

International Search Report and Written Opinion for corresponding application No. PCT/US2013/074628 mailed May 15, 2014.

RF ENERGY CONTROLLER AND METHOD FOR ELECTROSURGICAL MEDICAL DEVICES

This application is a filing under 35 U.S.C. §371 of International Patent Application PCT/US2013/074628, filed Dec. 12, 2013, which claims priority to U.S. application Ser. No. 13/713,648, filed Dec. 13, 2012.

TECHNICAL FIELD

The present invention relates generally to medical devices, and more particularly to control units that control the delivery of radio frequency (RF) energy to medical devices.

BACKGROUND

Barrett's esophagus is an abnormal change in the cells in a lower or bottom portion of the esophagus, which may be due to the esophagus receiving too much acid from the stomach. In some cases, the abnormal change may lead to cancer. To treat Barrett's esophagus, radio frequency (RF) energy, such as RF pulses, may be applied to skin cells or tissue at the surface of the esophagus. The application of the RF energy may ablate the tissue.

To ablate only the targeted tissue (i.e., the tissue at the surface), the RF pulses may be intense and short in duration. RF energy is typically not applied for longer than one second, and in many cases about one-half second or less. The duration that the RF energy is applied to the treatment site may be critical. Too much RF energy may cause harm to the patient, such as excessive burning of the tissue. Conversely, too little RF energy may fail to treat all of the abnormal skin cells. However, the duration of application of the RF energy may be difficult to control, particularly where the application is controlled through activation of a foot pedal.

Some RF generators may include and/or be housed with monitoring devices that monitor characteristics of the RF energy being output by the RF generator to prevent too much power from being output. Such monitoring devices may include digital processors and controls that are within the RF generators. However, many hospitals or other facilities have conventional RF generators that are not equipped with the monitoring devices. As such, a controller or control unit that is attachable to an RF generator and that controls delivery of RF energy from the generator to the medical device may be desirable.

BRIEF SUMMARY

The present disclosure describes a control unit that is configured to control delivery of radio frequency (RF) energy to a medical device. The control unit may include switching circuitry configured to switch between a closed state and an open state. In the closed state, the switching circuitry may be configured to permit RF energy received from an RF generator to be output by the control unit to the medical device. In the open state, the switching circuitry may be configured to prevent RF energy from being output by the control unit to the medical device. The control unit may also include energy measurement circuitry configured to measure an amount of RF energy delivered to the medical device; and switch the switching circuitry from the closed state to the open state when the amount of RF energy delivered to the medical device reaches a predetermined RF energy level.

The present disclosure also describes a method to control transmission of radio frequency (RF) energy from a RF generator to a medical device with a control unit coupled to the RF generator and the medical device. The method includes configuring switching circuitry of the control unit in a closed state. The method further includes receiving, with the switching circuitry in the closed state, RF energy from the RF generator; and transmitting, with the switching circuitry in the closed state, the RF energy to an output of the control unit. The method also includes determining, with energy measurement circuitry, the RF energy in the RF energy delivered to the medical device; and switching the switching circuitry, from the closed state to an open state upon the determined RF energy reaching a predetermined threshold energy level.

The present disclosure further describes a control unit configured to control delivery of radio frequency (RF) energy. The control unit includes an output coupled to a medical device configured to perform an ablation procedure; and an input coupled to an output of a RF generator configured to supply RF energy to the medical device for the ablation procedure. The control unit further includes switching circuitry coupled to the input and the output. The switching circuitry may be configured to permit the control unit to output RF energy received from the RF generator in a closed state, and to prevent the control unit from outputting the RF energy received from the RF generator in an open state. The switching circuitry may also include energy measurement circuitry coupled to the output. The energy measurement circuitry may be configured to determine an amount of RF energy being delivered to the medical device. The energy measurement circuitry may also be configured to switch the switching circuitry from the closed state to the open state when the amount of RF energy reaches a threshold level.

The present disclosure also describes another control unit that is configured to control delivery of radio frequency (RF) energy to a medical device. The control unit includes: a plurality of output terminals adapted for electric coupling with the medical device; selection circuitry configurable in a plurality of states, and when configured in each of the plurality of states, is configured to couple at least one and less than all of the plurality of output terminals to an output path of the control unit; and a controller configured to configure the selection circuitry in the plurality of states.

In addition, the present disclosure describes a method of controlling delivery of radio frequency (RF) energy with a control unit to a medical device. The method includes: outputting, with a controller of the control unit, a control signal to selection circuitry to configure the selection circuitry in one of a plurality of states, wherein the selection circuitry, when configured in each of the plurality of states, couples at least one and less than all of a plurality of output terminals to an output path of the control unit; and outputting the RF energy from the control unit to the medical device via the at least one and less than all of the plurality of output terminals being coupled to the output path by the selection circuitry.

DETAILED DESCRIPTION

Figure 1:
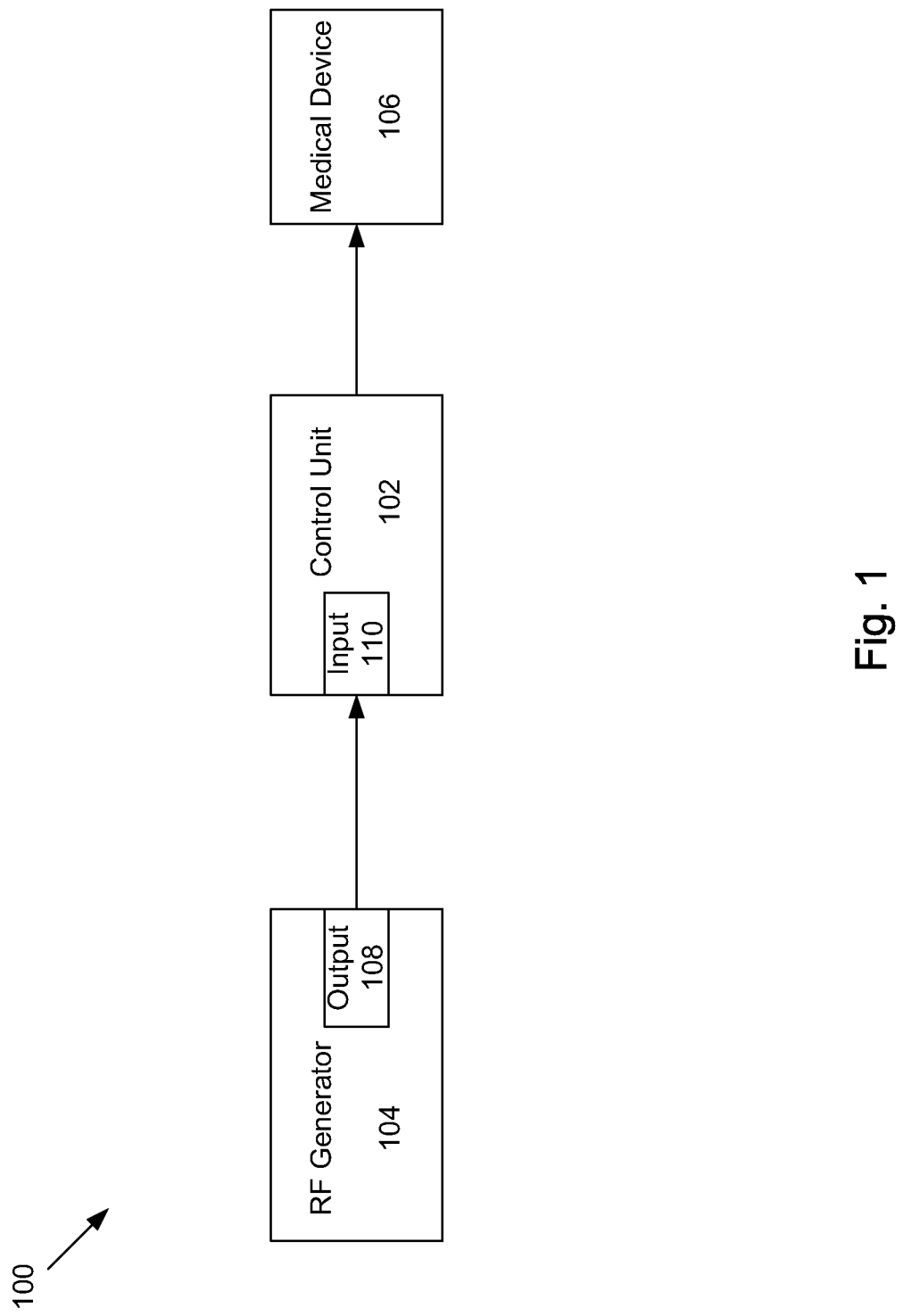
FIG. 1 shows a block diagram of a control unit coupled to a radio frequency (RF) generator and a medical device.

The present description describes a control unit that controls delivery of radio frequency (RF) energy to a medical device. The control unit may have an input or an input connector that is coupled to an output or an output connector of an RF generator that supplies RF energy for a medical procedure, such as tissue ablation. The control unit may receive RF energy and send the RF energy to a medical device that delivers the RF energy to a treatment site within a patient to perform the medical procedure. The control unit may measure the RF energy being delivered to the treatment site and determine when the RF energy reaches a predetermined level. When the RF energy reaches the predetermined RF energy level, the control unit may prevent further RF energy from being delivered to the medical device.

The predetermined RF energy level may be a selected amount of energy to be delivered to the treatment site for performing the medical procedure. When more than the predetermined RF energy level is delivered, harm or injury may be caused to the patient, such as burning of tissue at the treatment site. Alternatively, when less that the predetermined RF energy level is delivered, the medical procedure may be unsatisfactorily performed, such as by ablating an insufficient amount of tissue. As such, the control unit may be and/or provide a control and safety mechanism for the RF generator.

The control unit may be used with a conventional RF generator, such as a conventional electrosurgical unit (ESU), that does not include and/or have "built-in" similar control and safety mechanisms. The control unit may be a component separate to the RF generator. For example, the control unit may include a structure or "box" that is not housed within a housing the RF generator. Instead, the control unit may be housed outside of the RF generator. The control unit may have an input that may be connected or coupled to an output of the RF generator. Before performing the medical procedure, the control unit may be attached to the output of the RF generator. After the medical procedure is performed, the control unit may be detached from the output of the RF generator.

The housing of the control unit may be an enclosed structure that is configured to house circuitry and/or various circuit elements that measure the RF energy and determine when the RF energy reaches the predetermined level. The circuits may be hardware and/or analog circuits comprised of analog components that perform analog operations. The circuitry of the control unit may not include digital circuitry such as microprocessors, integrated circuits or other circuits that perform digital operations and/or execute software to perform energy measurement and timing operations. In alternative configurations, at least some of the circuits may include digital circuitry, such as microprocessors, microcontrollers, integrated circuits, digital hardware logic, or other similar types of digital circuits configured to perform digital operations and/or execute software to perform energy measurement and timing operations.

FIG. 1 shows a schematic diagram of an example medical system 100 that includes a control unit 102 that is configured to control delivery of RF energy from a RF generator 104 to a medical device 106. The RF generator 104, such as an electrosurgical unit (ESU), may be configured to supply the RF energy The RF energy may have characteristics, such as waveform, frequency, waveform, power, and/or amplitude characteristics, to perform an electrosurgical medical procedure, such as ablation or coagulation. To perform tissue ablation, for example, the RF energy may be a sine wave (such as a pulsed sine wave) having a frequency in a range of about 400 to 480 kilohertz (kHz), and a power of about 12 to 15 Watts. Other waveform, frequency, power, and/or amplitude characteristics may be used, which may depend on the medical procedure being performed.

The RF generator 104 may include an output 108 that may be configured to supply the RF energy to the connected system 100. In some example configurations, the output 108 may be a bipolar output connector. The type of connector may depend on the medical procedure being performed and/or the medical device 106 being used to perform the medical procedure. In addition or alternatively, the RF generator 104 may include and/or be adapted to connect to an input device (not shown), such as a foot pedal, that is used to generate the RF signals. The input device may be operated by the physician performing the medical procedure. For example, to generate the RF signals, the physician may activate and/or engage the input device. To cease generation of the RF signals, the physician may deactivate or disengage from the input device.

The control unit 102 may include an input 110 that is configured to connect to, attach to, and/or engage with the output 108 of the RF generator 104. When connected, attached, and/or engaged to the output 108, the control unit 102 may receive the RF energy from the RF generator 104. In some configurations, the input 110 may be removably attachable and/or connected to the output 108. For example, the input connector 110 may be attached or connected to the output connector 108, then detached or disconnected from the output connector 108, then reattached or reconnected to the output connector 108, and so on. The input connector 110 may be of any type or of any configuration that can connect and/or engage with the output connector 108 of the RF generator. In some configurations, the input connector 110 may be a banana connector or plug, although other types may be used and may depend on the configuration of the output connector 108 to which the input connector 110 is configured to connect.

The control unit 102 may be configured to switch between a closed state and an open state. When the control unit 102 is in the closed state, the control unit 102 may be configured to send the RF energy that the control unit 102 receives from the RF generator 104 to the medical device 106. In the open state, the control unit 102 may be configured to prevent the RF energy that the control unit 102 receives from the RF generator 104 from being sent to the medical device 106.

The control unit 102 may be configured to switch between the closed state and the open state by measuring an amount of energy being supplied to the medical device 106 from the RF generator 104. As the control unit 102 passes the RF energy that it receives from the RF generator 104 to the medical device 106, the amount of RF energy being supplied to the medical device 106 may increase to a threshold level. When the amount of RF energy is below the threshold level, the control unit 102 may be configured in the closed state, allowing the RF energy to be passed to the medical device 106. When the amount of RF energy reaches the threshold level, the control unit 102 may be configured to switch from the closed state to the open state, preventing the RF energy to be passed to the medical device 106.

The medical device 106 may include one or more components used to perform an electrosurgical medical procedure. For example, the medical device 106 may include one or more electrodes and/or one or more patches of electrode elements that are configured to receive the RF energy and provide the RF energy to a treatment site, such as tissue within a patient. The medical device 106 may further include a catheter or other elongate tubular body that may deliver the electrodes to the treatment site. In one example, the medical device 106 may be configured to treat Barrett's Esophagus and/or deliver RF energy in order to ablate tissue in the patient's esophagus.

Figure 2:
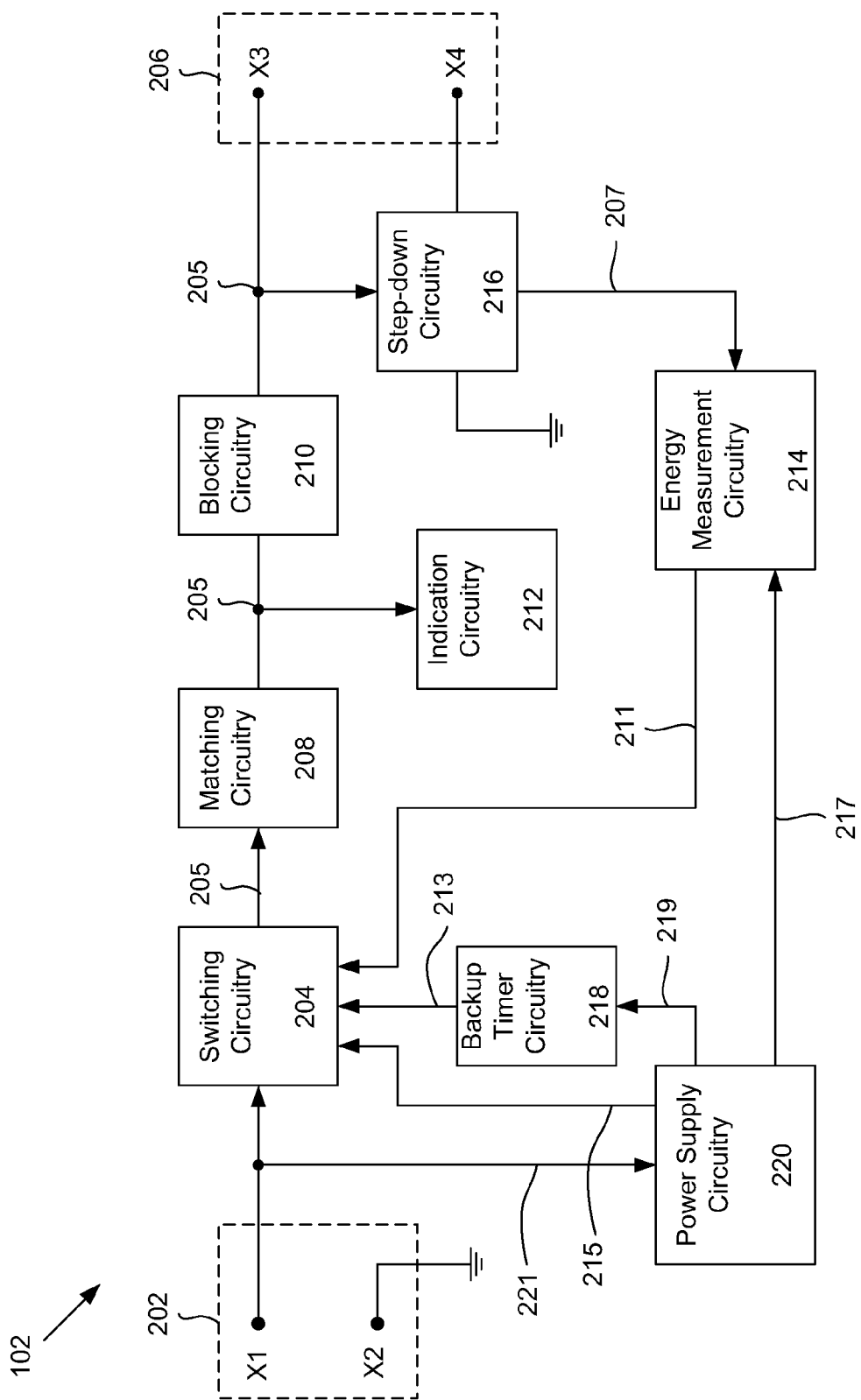
FIG. 2 shows a block diagram of the control unit.

FIG. 2 shows a block diagram of the control unit 102 in more detail. The control unit 102 may include an input 202 that is configured to receive RF energy from the RF generator 104. The input 202 may include a pair of terminals X1, X2, which may be configured or adapted to be connected to an output of the RF generator 104. For example, the terminals X1, X2 may be configured to be connected to a bipolar output of the RF generator 104. As shown in FIG. 2, one of the terminals X2 may be connected to a circuit ground. The other terminal X1 may be coupled to switching circuitry 204 and power supply circuitry 206.

The switching circuitry 204 may be configured to switch between a closed state and an open state, which in turn, may switch the control unit 102 between the closed state and the open state. When the switching circuitry 204 is in the closed state, the switching circuitry 204 may transmit the RF energy received from the input 202 along an output path 205 to an output 206 of the control unit 102. As shown in FIG. 2, the RF energy may pass through matching circuitry 208 and blocking circuitry 210 along the output path 205 before being provided to the output 206. Additionally, a small portion of the RF energy may be provided to indication circuitry 212 and energy measurement circuitry 214 via step-down circuitry 216 before being sent to the output 206. Alternatively, when the switching circuitry 204 is in the open state, the switching circuitry 201 may block or prevent transmission of the RF energy to the output 206 of the control unit 102.

As shown in FIG. 2, the output 206 may include a pair of terminals X3, X4 that are configured to be connected to the medical device 106 and provide RF energy to the medical device 106.

The matching circuitry 208, which may or may not be included or needed as a component of the control unit 102, may be used or configured to match the impedance of the load on the output 206 with the output impedance of the RF generator 104. In some example configurations, the matching circuitry 208 may include a matching transformer having a primary and secondary turns ratio to achieve the desired impedance matching.

In some situations, the impedance of the load at the output 206, which may be the impedance of the patient's tissue, may be about 25 ohms, and the load at the input, which may be the impedance of the output load of the RF generator 104, may be about 125 ohms, requiring an impedance change of a factor of about five. In these situations, the matching transformer may have 8 primary turns and 6 secondary turns, or if configured as an autotransformer, 14 primary turns and 6 secondary turns, which yields a turns ratio of about 2.3, or an impedance change of slightly over 5 (i.e., the turns ratio squared).

The blocking circuitry 210, which may or may not be included or needed as a component of the control unit 102, may be used or configured to block or prevent direct current (DC) and/or low-frequency components of the RF energy from being communicated to the output 206. The blocking circuitry 210 may be included because these RF signal components may cause harm to the patient during treatment. For example, low frequency components may shock the heart, which is located near the esophagus. The blocking circuitry 210 may include a capacitors coupled in series with the matching circuitry 208, and terminal X3 of the output 206, although other or additional circuitry may be used to block DC and/or low frequency components of the RF energy. To meet international standards, the blocking capacitor C2 may be less than 50 nF.

The indication circuitry 212, which may or may not be included as a component of the control unit 102, may be configured to output an indication that RF energy is being supplied to the medical device 106. In one example embodiment, the indication circuitry 212 includes a light emitting diode (LED) that outputs a light signal or is "on" when the RF signals are being sent to the output 206 and does not output a light signal or is "off" when RF energy is not being supplied to the output 206. In alternative example embodiments, the indication circuitry 212 may include circuitry in addition to or other than an LED, such as a speaker or a display device that outputs an audio and/or a visual signal to indicate whether RF energy is being supplied to the medical device 106. The indication circuitry 212 may be useful to and/or used by an operator of the RF generator 104, which may identify when to cease application of the RF energy (e.g., by removing bias on a foot pedal or other RF actuator) by observing the indication, such as when the LED turns from "on" to "off." The indication circuitry 214 may be coupled in shunt to the output path 205, and as shown in FIG. 2, may be coupled in shunt in between the matching circuitry 208 and the blocking circuitry 210. By being coupled in shunt, a small portion of the RF energy in the RF signals being supplied to the output 206 may be diverted to the indication circuitry 212, which the indication circuitry 212 may use to output the indication.

As shown in FIG. 2, the step-down circuitry 216 may be coupled in shunt to the output path 205 between the blocking circuitry 210 and the output 206. The step-down circuitry 216 may include a resistive network comprising one or more resistors. Based on the portion of the RF energy that the step-down circuitry 216 receives, the step-down circuitry 216 may be configured to provide one or more signals indicative of and/or proportional to the amount of RF energy being supplied to the output 206 and medical device 106. The step-down circuitry 216 may be configured to send the signals indicative of the supplied RF energy via connection 207 to the energy measurement circuitry 214. The connection 207 may include a plurality of connections configured to send a plurality of signals to the energy measurement circuitry 214. The plurality of signals may include signals indicative of, representative of, and/or proportional to the voltage and current being supplied to the medical device 106, which may then be used to generate signals indicative of the supplied RF energy. The step-down circuitry 216 may be coupled to both of the output terminals X3, X4 to generate the signals.

The energy measurement circuitry 214 may be configured to measure an amount of energy, such as an amount of total energy that is being supplied to the medical device 106 via the output 206. The energy measurement circuitry 214 may further be configured to determine when the amount of RF energy reaches a threshold level. The threshold level may be a predetermined level and/or may indicate an energy level that, when met, may be a sufficient portion of a medical treatment. The energy measurement circuitry 214 may be coupled to the switching circuitry 204 via connection 211 such that when the amount of energy reaches the threshold level, the energy measurement circuitry 214 may cause the switching circuitry 204 to switch from the closed state to the open state, which may prevent RF energy received from the RF generator 104 from being sent to the medical device 106.

The control unit 102 may further include backup timer circuitry 218. The backup timer circuitry 218 may be configured to switch the switching circuitry 204 from the closed state to the open state when a period of time elapses. For example, the backup timer circuitry 218 may be coupled to the switching circuitry 204 via a connection 213, such that when the period of time elapses, the backup timer circuitry 218 may cause the switching circuitry 204 to switch from the closed state to the open state, preventing RF energy received from the RF generator 104 from being sent to the medical device 106.

In some configurations, the period of time may be a predetermined period of time that is greater than an expected and/or an anticipated period of time for the RF energy being supplied to the medical device 104 to reach the threshold level. In this sense, the backup timer circuitry 218 may function as a safety feature of the control unit 102. In particular, the backup timer circuitry 218 may ensure that RF energy may not be supplied to the treatment site for an extended period of time such that harm may be caused to the patient, particularly if the switching circuitry 204 does not switch from the closed state to the open state when the supplied RF energy reaches the threshold level. If the switching circuitry 204 does not switch when the RF energy reaches the threshold level—such as due to a malfunction or failure by the energy measurement circuitry 214 and/or by the switching circuitry 204—then the backup timer circuitry 218 may serve as backup or secondary control circuitry that turns the switching circuitry 204 to the open state. When the backup timer circuitry 218 switches the switching circuitry 204 to the open state, the backup timer circuitry 218 may prevent the RF energy from being supplied to the treatment site for too long of a period of time. In one example, the predetermined period of time may be about one second, which may be greater than an expected and/or anticipated period of time of about 0.5 seconds for the supplied RF energy to reach the threshold level.

The control unit 102 may further include power supply circuitry 220. As shown in FIG. 2, the power supply circuitry 220 may be coupled to the input terminal X1 via a connection 221. A portion of the RF energy received from the RF generator 104 by the input 202 may be sent to the power supply circuitry 220, and a remaining portion may be sent to the switching circuitry 204. The portion of the RF energy sent to the power supply circuitry 220 may be used by the power supply circuitry 220 to power active elements of the circuitry components of the control unit 102. In this way, the control unit 102 may be a self-powering device or apparatus in that the control unit 102 does not receive power from a separate power supply. Instead, the control unit 102 may power itself by generating its own power, using the RF energy that the control unit 102 receives from the RF generator 104.

Figure 3:
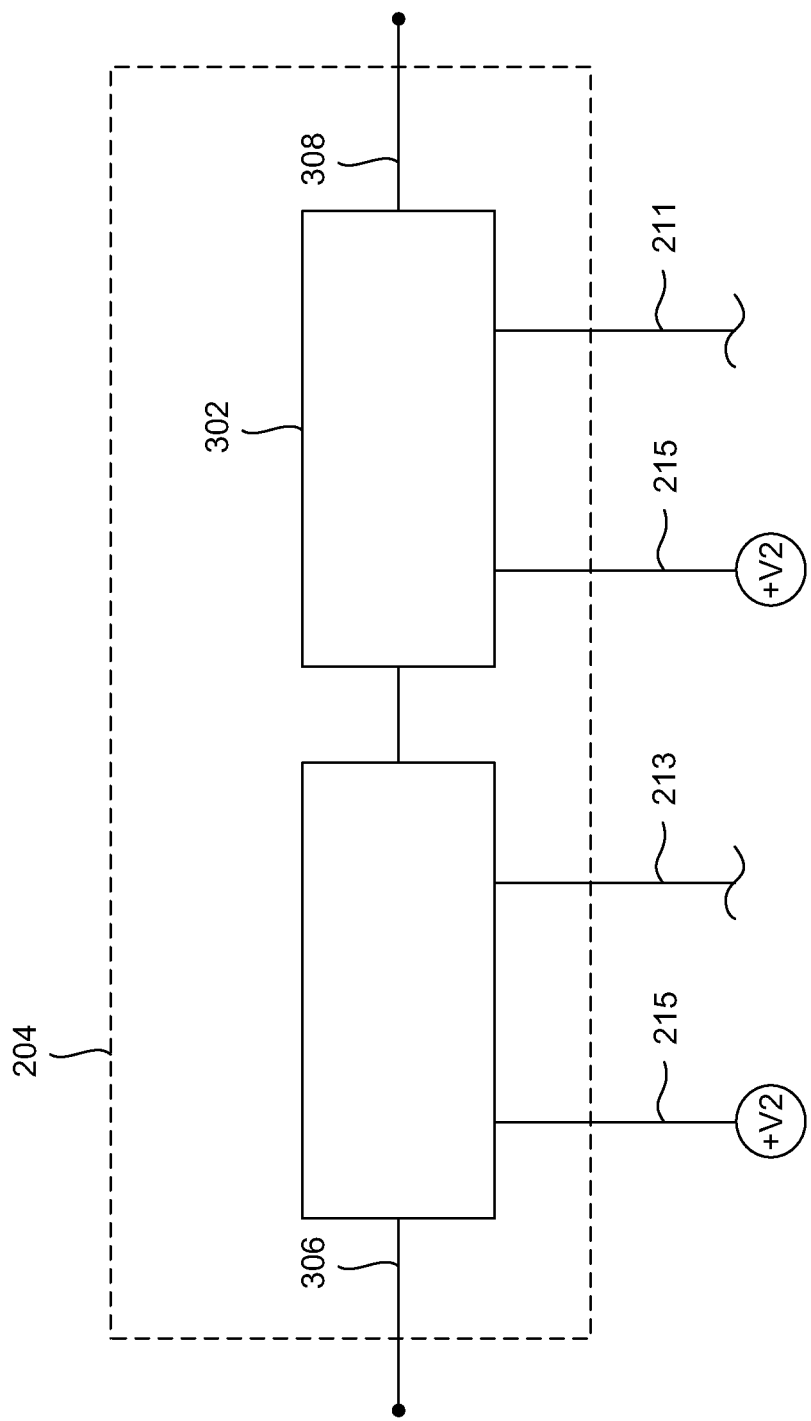
FIG. 3 shows a circuit diagram of example switching circuitry in the control unit.

FIG. 3 shows a circuit diagram of an example circuit configuration of the switching circuitry 204. The switching circuitry 204 may include a first switch 302 connected in series with a second switch 304. The switches 302 may switch the switching circuitry 204 between the closed state and the open state when the energy measurement circuitry 214 detects that the RF energy being supplied to the medical device 106 has reached the threshold level. The other switch 304 may switch the switching circuitry 204 between the closed state and the open state when the period of time determined by the backup timer circuitry 218 elapses. For example, the first switch 302 may be coupled to the energy measurement circuitry 214 via connection 211 such that when the amount of energy supplied to the medical device 106 reaches the threshold level, the energy measurement circuitry 214 may cause the first switch 302 to switch from a closed state to an open state, which in turn may configure the switching circuitry 204 in the open state and prevent RF energy from being supplied to the medical device 106. The second switch 304 may be coupled to the backup timer circuitry 218 via connection 213 such that when a period of time determined by the backup timer circuitry 218 elapses, the backup timer circuitry 218 may cause the second switch 304 to switch from a closed state to an open state, which in turn may configure the switching circuitry 204 in the open state and prevent RF energy from being output from the control unit 102. By being connected in series, only one, or alternatively both, of the switches 302, 304 may be in the open state to configure the switching circuitry 204 in the open state and prevent RF energy from being supplied to the medical device 106.

The switching circuitry 204 may further include an input 306 coupled to the input 202 of the control unit 102 and the second switch 304, and an output 308 coupled to the output path 205 and the first switch 302. When both the first switch 302 and the second switch 304 are in the closed state, the RF signals received from the input 202 of the control unit 102 may be communicated from the input 306, through the second switch 304 and the first switch 302, to the output 308.

In some example embodiments, the first switch 302 and/or the second switch 304 may be relays. In a preferred embodiment, the relays 302 and 304 may be double pole double throw relays, although in alternative embodiments, one or both of the relays 302, 304 may be a different type, such as single pole single throw, single pole double throw, or double pole single throw, as examples.

The first relay 302 may be coupled to the energy measurement circuitry 214 via the connection 211. The energy measurement circuitry 214 may be configured to activate the first relay 302 when the energy measurement circuitry 214 detects that the RF energy being supplied to the medical device 106 has reached the threshold level, which may switch the first relay from the closed state to the open state. The first relay 302 may also receive a positive power supply signal +V2 to activate the first relay 302. The second relay 304 may be coupled to the backup timer circuitry 218 via the connection 213. In some configurations, when the period of time elapses, the backup timer circuitry 218 may activate the second relay 304, which may switch the second relay 304 from the closed state to the open state. In alternative configurations, the second relay 304 may be in the closed state when activated by the backup timer circuitry 218. In these alternative configurations, the backup timer circuitry 218 may activate the second relay 304 to maintain the second relay 304 in the closed state until the time period elapses, at which point the backup timer circuitry 218 may deactivate the second relay 304 to switch the second relay 304 to the open state. The first relay 302 may also receive the positive power supply signal +V2 to activate the first relay 302.

The switching circuitry 204 is not limited to using double pole double throw relays, and alternative embodiments may include other types of relays that switch from being closed to being open when activated may be used. However, the use of relays having two poles may provide extra safety compared to single pole relays in that when the electromagnetic device is activated, if one pole opens but the other pole malfunctions and remains closed, the relay is still switched to the open state. In other words, both poles must malfunction for the switch to stay closed. In other alternative embodiments, the switching circuitry 202 may include switches or switching devices other than relays, such as transistors or other semiconductor and/or solid state devices.

Figure 4:
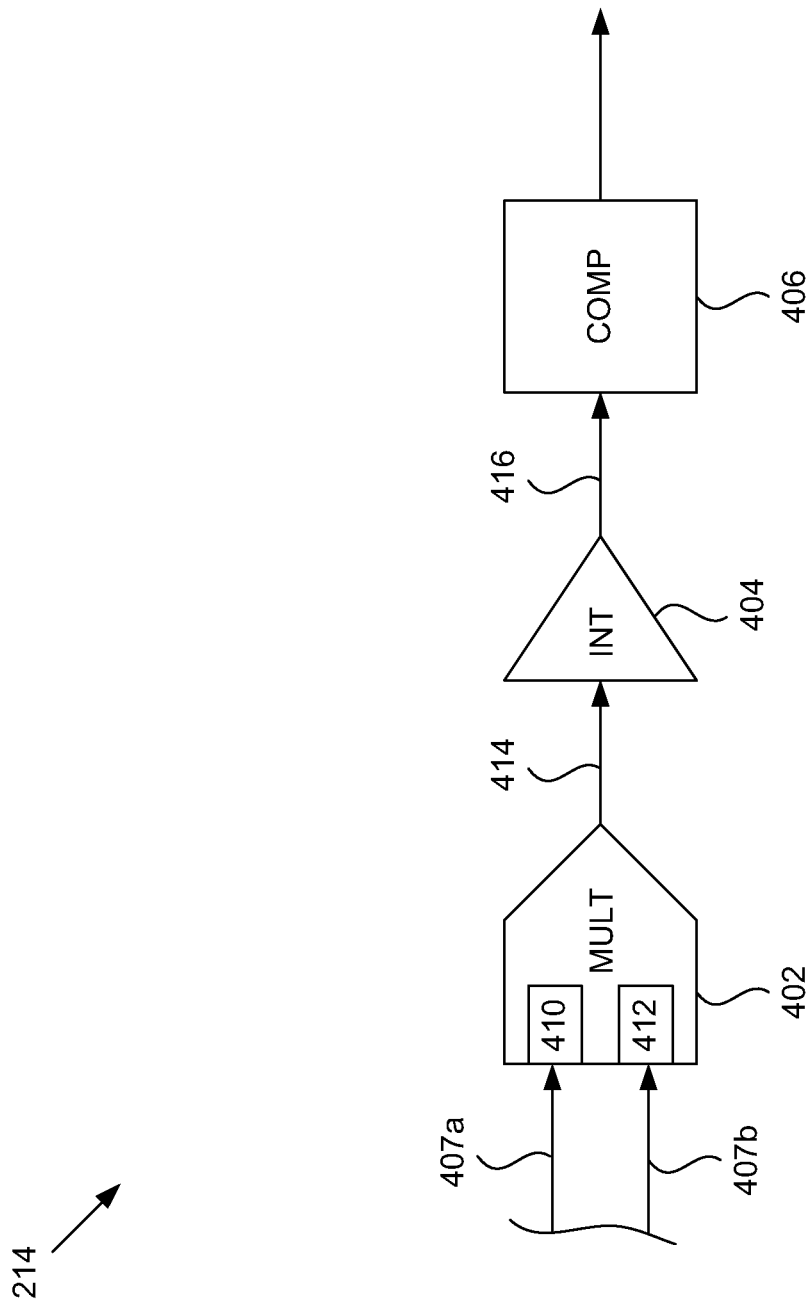
FIG. 4 shows a block diagram of example energy measurement circuitry in the control unit.

FIG. 4 shows a block diagram of the energy measurement circuitry 214 of the control unit 102 in more detail. The energy measurement circuitry 214 may be configured to determine an amount of RF energy, such as an amount of total RF energy, that is supplied to the medical device 106. The energy measurement circuitry 214 may also determine whether the amount of RF energy has reached a threshold level, and in response to the determination, may generate and/or output a signal that switches the switching circuitry 204 from the closed state to the open state. To perform these actions or functions, the energy measurement circuitry 214 may include three main circuit elements—multiplier circuitry 402, integrator circuitry 404, and comparator circuitry 406.

The multiplier circuitry 402 may include inputs 410, 412, which may be coupled to the output path 205 via the step down-circuitry 216 and the connection 207. As previously described, the connection 207 may include multiple connections configured to supply a plurality of signals to the energy measurement circuitry 214 that are indicative of, representative of, and/or proportional to the voltage and current being supplied to the medical device 106. As shown in FIG. 4, the connection 207 may include a first connection 407a and a second connection 407b. In one example configuration, signals proportional to the voltage being output from the control unit 102 and/or supplied to the medical device 106—hereinafter referred to as voltage signals—may be sent to the first input 410 via the first connection 407a. Signals proportional to the current being output from the control unit 102 and/or supplied to the medical device 106—hereinafter referred to as current signals—may be sent to the second input 412 via the second connection 407b. The multiplier circuitry 402 may be configured to multiply the voltage signals with the current signals. Based on the multiplication of the voltage signals and the current signals, the multiplier circuitry 402 may be configured to generate a signal indicative of instantaneous power being supplied to the medical device 106.

The multiplier circuitry 402 may be configured to output the signal indicative of the instantaneous power to the integrator circuitry 404 via a connection 414. The integrator circuitry 404 may be configured to receive the signal output from the multiplier circuitry 402 or receive signals based on the signals output from the multiplier circuitry 402, such as signals that are scaled down from the signals output from the multiplier circuitry 402. Upon receipt, the integrator circuitry 404 may be configured to generate and output signals indicative of the average power or total energy being supplied to the medical device 106.

The comparator circuitry 406 may be configured to receive the signals output from the integrator circuitry 404 or receive signals based on the signals from the integrator 404, such as signals that are scaled down from the signals output from the integrator circuitry 404 via connection 416. Upon receipt, the comparator circuitry 406 may be configured to compare the received signals with a reference value, such as a predetermined reference value, proportional to a threshold energy level, the threshold energy level being a RF energy level that corresponds to a portion of the treatment. By comparing the received signals with the reference value, the comparator circuitry 406 may be configured to determine whether the RF energy being supplied to the medical device 106 is below or has reached the threshold energy level.

Based on the comparison of the signals received from the integrator circuitry 406 and the reference value, the comparator circuitry 406 may output a signal that switches the switching circuitry 204, including the first switch 302, between the closed and open states. For example, when the comparator circuitry 406 determines that the received signal is less than or does not exceed the reference value, the comparator circuitry 406 may be configured to not output a signal, or alternatively may be configured to output a signal at a level that configures the first switch 302 in the closed state. In particular, the comparator circuitry 406 may not output a signal, or alternatively may output a signal at a level that does not induce current through the electromagnetic device 310 (FIG. 3), which positions the first switch 302 in the closed state. Alternatively, when the comparator circuitry 406 determines that the received signal meets or reaches the reference value, the comparator circuitry 406 may be configured to output a signal that configures the first switch 302 in the open state. The signal that is output by the comparator circuitry 406 when the received signal reaches the predetermined value may induce current through the electromagnetic device 310 (FIG. 3), which may energize or activate the electromagnetic device 310 and switch the first switch 302 (FIG. 3) to the open state.

Figure 5:
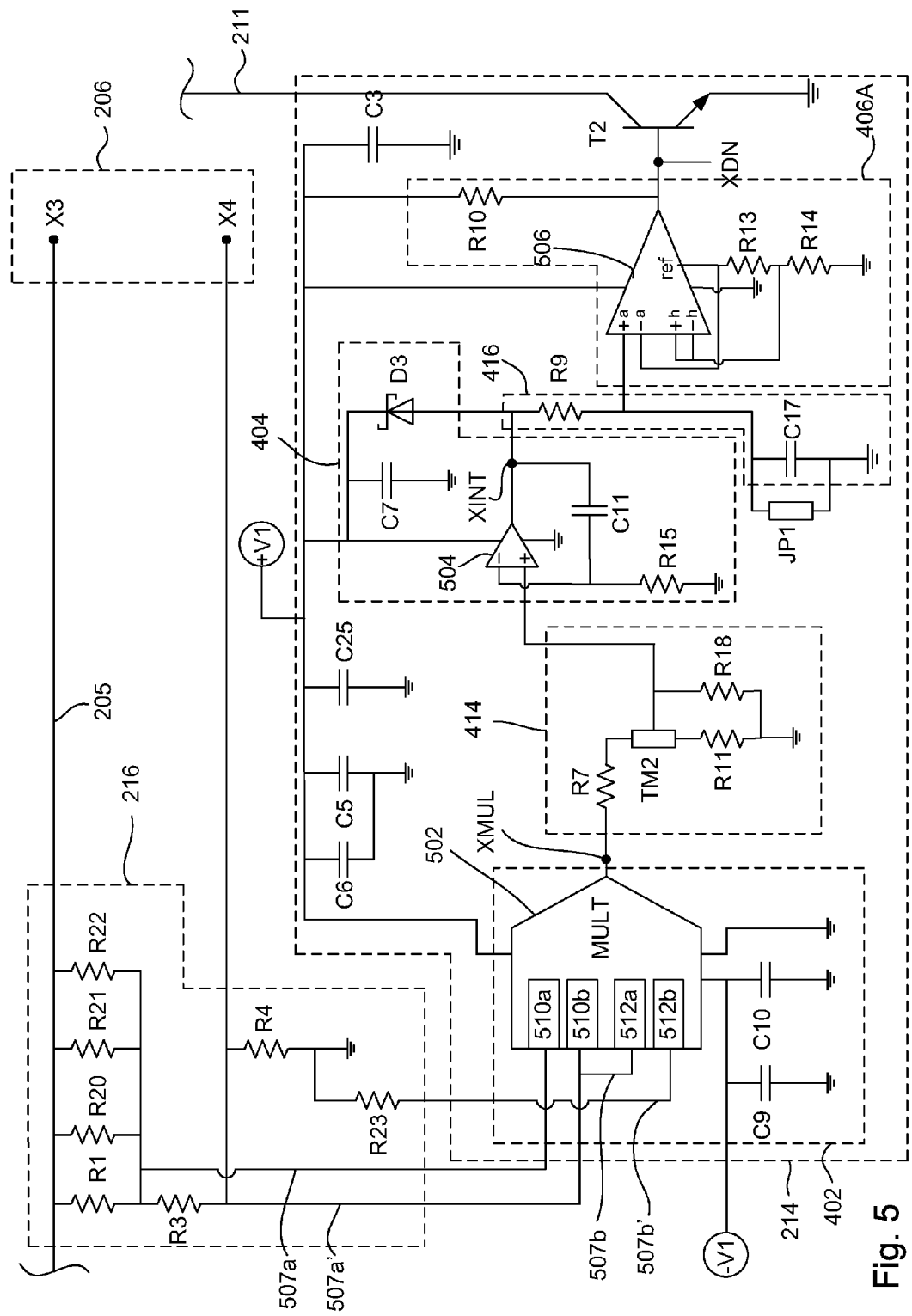
FIG. 5 shows a circuit diagram of an example circuit implementation of the energy measurement circuitry.

FIG. 5 shows a circuit schematic of an example circuit implementation of the step-down circuitry 216 and an example circuit implementation of the energy measurement circuitry 214 coupled to the output path 205 and the output 206. The step-down circuitry 216 may include a resistive network, which may include resistors R1, R3, R4, R20, R21, R22, and R23. The resistive network may be coupled to terminals X3 and X4 of the output 206 in such a way as to provide signals scaled down from the output path 205 that are proportional to the voltage and current being supplied to the medical device 106 to the energy measurement circuitry 214.

In the example circuit implementation shown in FIG. 5, the resistors R1, R3, R20, R21, and R22 may be configured as a voltage divider, that may yield a first voltage drop by resistors R1, R20, R21, and R22, which may be coupled to the output path 205 and connected in parallel, and may also yield a second voltage drop by resistor R3, which may be connected to the parallel connection of R1, R20, R21, and R22. A first voltage signal generated by the first voltage drop may be sent to the energy measurement circuitry 214 via connection 507a. A second voltage signal generated by the second voltage drop may be sent to the energy measurement circuitry 214 via connection 507a'. The first and second voltage signals may form a differential voltage signal that is received by the energy measurement circuitry 214, and that is indicative of, representative of, and/or proportional to the voltage being supplied to the medical device. Four resistors, R1, R20, R21, R22 connected in parallel may be used to reduce or minimize heat generated in the voltage divider, although more or fewer than four resistors may be used.

Resistor R4 may be configured to generate a pair of signals on connections 507b and 507b', forming a differential signal that is proportional to the current being supplied to the medical device 106. The resistor R23 may be included to match input impedances of the multiplier circuitry 402. The signal generated on 507b' may have a voltage that is the voltage drop yielded by resistor R4

An example multiplier may be an Analog Devices AD835 4-Quadrant Multiplier, although other multipliers may be used. The multiplier 502 may have a pair of differential inputs, including a first differential input 510a, 510b to receive the differential voltage signal via connections 507a, 507a', and a second differential input 512a, 512b to receive the differential current signal via connections 507b, 507b'. The multiplier 510 may be configured to multiply the differential voltage signal with the differential current signal to generate an output signal indicative of and/or proportional to the instantaneous RF power being supplied to the medical device 106. The multiplier 510 may output the output signal to the integration circuitry 404 at the output XMUL.

As shown in FIG. 5, the multiplier 502 may receive power, such as positive voltage +V1 and negative voltage −1V, from the power supply circuitry 220. Capacitors C5, C6, C9, C10, and C25 may be included to reduce noise.

The output XMUL of the multiplier circuitry 402 may be coupled to the integrator circuitry 404 via connection 414. The connection 414 may include a voltage divider that is configured to scale down the output of the multiplier circuitry 402. The voltage divider may include a resistor R7, a variable resistor (or a trimmer resistor or a potentiometer) TM2, and resistors R11 and R18. The variable resistor TM2 may be configured to scale down the output of the multiplier circuitry 402 at XMUL in a range of about 25% to 50%, although other ranges are possible. The variable resistor TM2 may provide the voltage divider with variable scalability to calibrate the energy measurement circuitry 214 as a whole. The resistor R18 may be included to draw a relatively small amount of current through a wiper component of the variable resistor TM2 to reduce or minimize oxide accumulation or build up.

The integrator circuitry 404 may include an operational amplifier (op-amp) 504, which may be configured as a non-inverting op-amp integrator. An example op-amp 504 may be a National Semiconductor LM6211 low noise rail-to-rail (RRO) operation amplifier. The integrator circuitry 404 may include a resistor R15 in conjunction with a feedback capacitor C11 may determine a resistor-capacitor (RC) time constant that, in turn, determines an integration gain constant of the integration circuitry 404.

The integrator circuitry 404 may further include reset circuitry, which may include a diode D3, such as a Schottky diode, that provides a discharge path for charge stored across the capacitor C11 to discharge. When the power supply circuitry 220 (FIG. 2) is no longer supplying power to the other components of the control unit 102 (e.g., because the physician or operator removed his/her foot from the RF generator 104 and the RF generator 104 is no longer supplying RF energy to the power supply circuitry 220), the diode D3 may become forward biased, and charge stored at the output XINT may discharge through the diode D3 to the connection 514, and to the power supply circuitry 220. A capacitor C7 may be included to reduce noise.

As previously described, the integrator circuitry 404 may output the signals to the comparator circuitry 406 via connection 416. In the example circuit implementation shown in FIG. 5, the connection 416 may include a low-pass filter having a resistor R9 connected with a capacitor C17, to reduce noise before the signals are supplied to the comparator circuitry 406. The comparator circuitry 406 may receive the signals from the connection 416 and, based on the levels of the received signals, determine whether the RF energy being supplied to the medical device 106 has reached the threshold level.

FIG. 5 shows an example comparator circuit 406A that may be used for the comparator circuitry 406 shown in FIG. 4. The example comparator circuit 406A may include a comparator 506 which may be a packaged chip or component and be powered by the positive power supply signal +V1. An example comparator 506 may be a National Semiconductor LMP7300 micropower precision comparator, although other types of comparators may be used. The comparator 506 may include a reference terminal "ref," which may set or provide a reference level or value for the comparator 506. The reference terminal "ref" may be connected or tied to a negative input terminal −a of the comparator 506.

In operation, when the level of the signals received at a positive input terminal +a reaches the reference level at the negative input terminal −a, the comparator 506 may be configured to generate an output signal at an output XDN (if the comparator 506 has an open collector or similar output). A resistor R10 may be included at the output XDN to generate a logic "high" signal. The output signal generated by the comparator 506 may be applied to a switch T2, which turns the switch T2 from an "off" state to an "on" state. The switch T2 may have a terminal connected to the connection 211 (FIG. 2), which is connected to the terminal A1 of the electromagnetic device 310. Turning switch T2 "on" may switch the first switch 302 from the closed state to the open state. In some example configurations, the switch T2 may be a semiconductor device, such as a transistor. An example transistor may be a NZT7053 NPN Darlington transistor.

The comparator 506 may further include hysteresis inputs +h, −h. The hysteresis inputs +h, −h may provide hysteresis functionality to the comparator 506 to prevent the comparator 506 from providing a fluctuating output once the comparator 506 outputs a signal to turn the switch T2 "on." Resistors R13 and R14 may be used to set the hysteresis value.

Figure 5A:
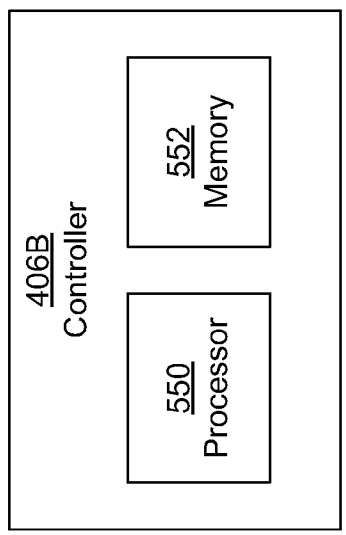
FIG. 5A shows a block diagram of an example implementation of comparator circuitry alternative to the example circuit implementation shown in FIG. 5.

In alternative configurations, the comparator circuitry 406 may be include and/or be implemented using a controller 406B shown in FIG. 5A instead of the comparator 406A shown in FIG. 5. The controller 406B may include a processor 550 configured to perform the functions of the comparator circuitry 406. The controller 406B may also include a memory 552, which may be configured to store information for the processor 550 to use to perform the functions of the comparator circuitry 406. For example, the memory 552 may store computer executable instructions that the processor 550 may execute to perform the functions of the comparator circuitry 406. In addition or alternatively, the memory 552 may store a threshold or reference value that the processor 550 may access and compare with the RF energy being supplied to the medical device 104 to determine whether the supplied RF energy has reached the threshold level.

In addition or alternatively, the multiplier circuitry 402 may be implemented as a controller having a processor and a memory, instead of being implemented using the hardware configuration shown in FIG. 5. This alternative configuration may be similar to the configuration of the controller 406B shown in FIG. 5A. However, where the controller 406B is used for the comparator circuitry 406, using the hardware components shown in FIG. 5 instead of a controller for the multiplier circuitry 402 may be desirable or advantageous in that it may allow the sampling rate of the controller 406B to be kept low, resulting in a less complex controller and/or a controller that consumes less power for the comparator circuitry 406.

In some example circuit implementations, the energy measurement circuitry 214 may further include a jumper JP1 connected in parallel with the capacitor C17. The jumper JP1 may be configured in the energy measurement circuitry 214 such that if the jumper JP1 is shorted, the capacitor C17 may be shorted, which may prevent signals output from the integrator circuitry 404 and/or transmitted via the connection 416 from being received by the comparator circuitry 406. Shorting the jumper JP1 may allow a user or operator to perform one or more calibrations or activities on the control unit 102, such as calibration of the backup timer circuitry 218.

Table 1 provides exemplary component values for the circuit components of the circuitry implementations of the stepdown circuitry 216 and the energy measurement circuitry 214 shown in FIG. 5.

TABLE 1

| | |
|---|---|
| R1 | 5.1 kΩ |
| R3 | 50 Ω |
| R4 | 1 Ω |
| R20 | 5.1 kΩ |
| R21 | 5.1 kΩ |
| R22 | 5.1 kΩ |
| R23 | 47 Ω |
| C9 | 1 µF |
| C10 | .01 µF |
| R7 | 75 Ω |
| TM2 | 50 Ω |
| R11 | 27 Ω |
| R18 | 1.5 kΩ |
| R15 | 20 kΩ |
| C11 | 2.2 µF |
| C7 | 0.1 µF |
| R9 | 10 kΩ |
| C17 | 0.1 µF |
| R13 | 300 Ω |
| R14 | 2.2 kΩ |
| R10 | 10 kΩ |
| C6 | 1 µF |
| C5 | 0.01 µF |
| C25 | 0.1 µF |
| C3 | 0.1 µF |

Figure 6A:
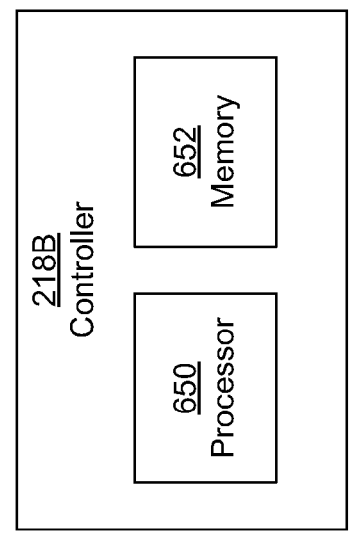
FIG. 6A shows a block diagram of an example implementation of the backup timer circuitry alternative to the example circuit implementation shown in FIG. 6.
Figure 6:
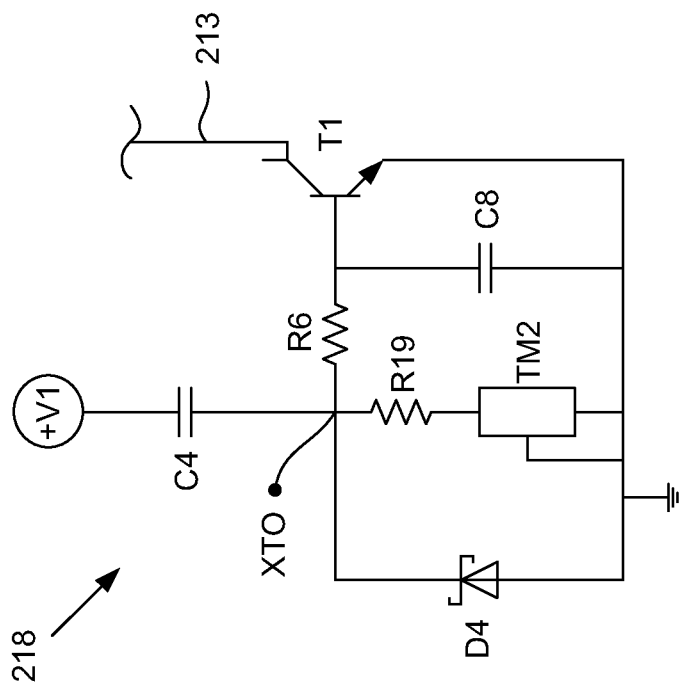
FIG. 6 shows a circuit diagram of an example circuit implementation of backup timer circuitry in the control unit.

FIG. 6 shows a circuit schematic diagram of an example circuit implementation of a backup timer circuit 218A that may be used for the backup timer circuitry 218. The backup timer circuit 218A may include a capacitor C4 connected to a parallel connection including a resistor R19, a variable resistor TM2, a resistor R6, and a base-emitter junction of a transistor T1. As previously described, the backup timer circuitry 218 may be configured to switch the switching circuitry 204 from the closed state to the open state when a period of time elapses. In the example circuit implementation shown in FIG. 6, the period of time may be determined by a resistor-capacitor (RC) time constant set by a capacitance of the capacitor C4 and an impedance of the parallel connection of R19 and TM2 with R6 and the base-emitter junction of T1. In one example configuration, the transistor T1 may be a NZT7053 NPN Darlington transistor, although other types of transistors may be used. The variable resistor TM2 may be used, rather than a resistor with a fixed resistance, in order to provide an adjustable impedance for calibration. The collector of the transistor T1 may be coupled to the electromagnetic device 315 of the second switch 304 (FIG. 3) via the connection 213.

The example circuit implementation of the backup timer circuit 218A may further include a capacitor C8 coupled to the base of the transistor T1 and ground. The capacitor C8 may be included to reduce noise generated in the backup timer circuit 218A. The backup timer circuit 218A may also include a diode D4, such as a Schottky diode, connected to a node connecting the capacitor C4, the resistor R19, and the resistor R6. The diode D4 may serve as a discharge path for the capacitor C4, such as when the power supply circuitry 220 is unpowered and the positive power supply signal +V1 is not being sent to the backup timer circuit 218A. Providing the diode D2 to serve as a discharge may allow the backup timer circuit 218A to reset quickly between activations.

In operation, when the power supply circuitry 220 is unpowered and the positive power supply signal +V1 is not being supplied to the backup timer circuit 218A, there is zero volts across the capacitor C4 since any charge stored in the capacitor C4 may discharge through the diode D4 to ground. When the power supply circuitry 220 powers up, the positive power supply signal +V1 is sent to an end of the capacitor C4, supplying a voltage to the capacitor C4. At this time, the other end of the capacitor C4 (i.e., at node XTO) is also at the voltage supplied by the positive power supply signal +V1 because the capacitor C4 may not change its voltage instantaneously (i.e., the capacitor C4 has to charge for its voltage to change). The voltage supplied by the positive power supply signal +V1 may turn the transistor T1 "on," which may induce current through the electromagnetic device 315 (FIG. 3), and switch the second switch 304 to the closed state.

After the power supply circuitry 220 initially supplies the positive power supply signal +V1 to the backup timer circuit 218A, the voltage at node XTO may decay from the voltage of the positive power supply signal +V1 at a rate, such as an exponential rate, determined by the RC time constant. The voltage at node XTO may decay to a level that turns the transistor T1 "off." When the transistor T1 is "off," current is no longer induced through the electromagnetic device 315, and the second switch 304 switches to the open state.

Under typical operation of the RF generator 104, the physician or operator of the RF generator will cease output of the RF signals from the RF generator 104, such as by removing his/her foot from a foot pedal. As previously described, the RF signals from the RF generator 104 are used to power the power supply circuitry and generate the power supply signals that are supplied to the other components of the control unit 102. As such, when the output of the RF signals is ceased, the positive power supply signal +V1 is no longer supplied to the backup timer circuit 218A. At this time, any remaining or residual charge stored in the capacitor C4 may discharge through the diode D4, yielding a zero voltage drop across the capacitor C4. The backup timer circuit 218A may then be ready to receive the positive power supply signal +V1 from the power supply circuitry 220, in which the backup timer operation may be repeated. Table 2 provides exemplary component values for the circuit components of the circuit implementation of the backup timer circuitry 218A shown in FIG. 6.

TABLE 2

| | |
|---|---|
| C4 | 20 µF |
| R19 | 1 kΩ |
| TM1 | 50 kΩ |
| R6 | 47 kΩ |
| C8 | 0.01 µF |

In an alternative implementation, the backup timer circuitry 218 may include and/or be implemented using a controller 218B shown in FIG. 6B instead of the backup timer circuit 218A shown in FIG. 6. The controller 218B may include a processor 650 that is configured to perform the functions of the backup timer circuitry 218. The controller 218B may also include a memory 652, which may be configured to store information for the processor 650 to use to perform the functions of the backup timer circuitry 218. For example, the memory 652 may store computer executable instructions that the processor 650 may execute to perform the functions of the backup timer circuitry 218. In addition or alternatively, the memory 652 may store a threshold or reference count value, which the processor 650 may access and/or use to determine whether the backup period of time has elapsed or expired.

For configurations where both the comparator circuitry 406 and the backup timer circuitry 218 include and/or are implemented using controllers, the controllers may be the same component or separate, different components. Various configurations or combinations of configurations of the comparator circuitry 406 and the backup timer circuitry 218 are possible.

Figure 7:
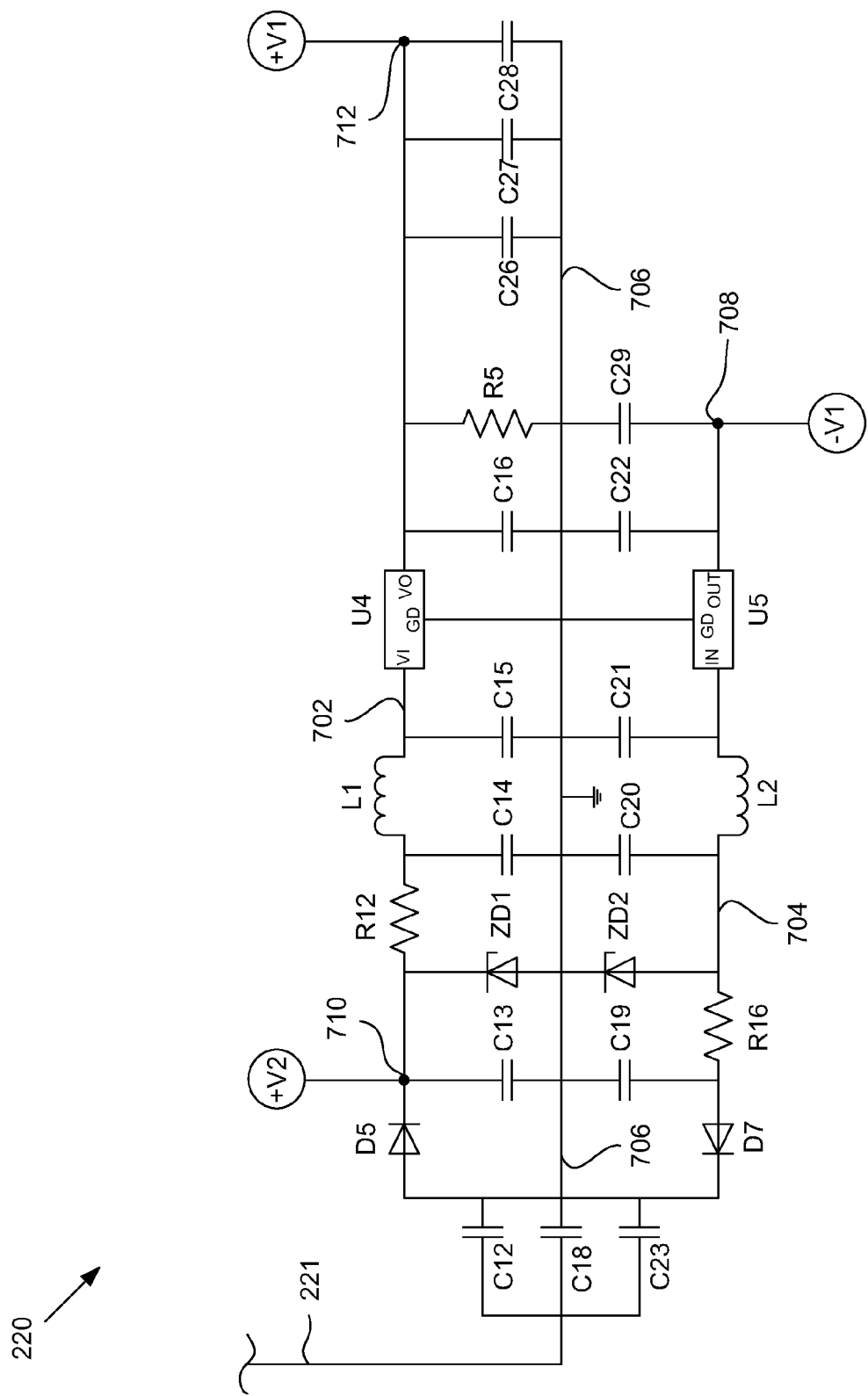
FIG. 7 shows a circuit diagram of an example circuit implementation of power supply circuitry in the control unit.

FIG. 7 shows an example circuit implementation of the power supply circuitry 220. The power supply circuitry 220 may be configured to generate and output one or more positive power supply (e.g., DC power supply) signals and/or one or more negative power supply (e.g., DC power supply) signals.

The power supply circuitry 220 may include capacitors C12, C18, and C23 coupled to the connection 221 and the first and second portion 702, 704. The capacitors C12, C18, C23 may be configured to step-down the voltage of the RF signals received from the terminal X1 via connection 221. In alternative configurations, components other than capacitors, such as resistors, may be used. The diodes D5, D7 may provide rectification, such as half-wave rectification, to convert the RF (i.e., AC) signals into rectified AC signals.

The power supply circuitry 220 may include a resistor R16 and a zener diode ZD2 to function as a generally imprecise voltage regulator to prevent the voltage generated at the node between the resistor R16, the zener diode ZD2, and an inductor L2 from damaging a voltage regulator U5. A pi network, formed by the inductor L2 and capacitors C20, C21, may reduce noise before signals are received by the voltage regulator U5. An example voltage regulator U5 may be a National Semiconductor 79L05 voltage regulator. Capacitors C22 and C29 may provide further noise filtering.

A zener diode ZD1, in conjunction with the step down capacitors C12, C18, C23, may function as a generally imprecise voltage regulator for the voltage generated at node 710. A resistor R12 may be coupled to node 710 to further scale down the voltage to prevent a regulator U4 from being damaged. A pi network, formed by an inductor L1 and capacitors C14 and C15, may reduce noise before signals are received by the voltage regulator U4. The voltage regulator U4 may be configured to output a substantially regulated second positive power supply +V1 at node 712. The output of the regulator U4 may discharge through a resistor R5 after the power supply circuitry 220 powers down. Capacitors C13, C19, C16, C26, C27, and C28 may be included in the power supply circuitry 220 to further reduce noise.

Table 3 provides exemplary component values for the circuit components of the circuit implementation of the power supply circuitry 220 shown in FIG. 7.

TABLE 3

| | |
|---|---|
| C12 | 1 nF |
| C18 | 1 nF |
| C23 | 1 nF |
| D5 | RS2B |
| D7 | RS2B |
| C13 | 1 µF |
| C19 | 1 µF |
| R16 | 150 Ω |
| R12 | 200 Ω |
| C14 | 1 µF |
| C20 | 1 µF |
| L1 | 30 µH |
| L2 | 30 µH |
| C15 | 1 µF |
| C21 | 1 µF |
| U4 | MCP1703CB |
| U5 | 79L05 |
| C16 | 1 µF |
| C22 | 1 µF |
| R5 | 4.7 kΩ |
| C29 | 0.1 µF |
| C26 | 0.1 µF |
| C27 | 0.1 µF |
| C28 | 0.1 µF |

Figure 8:
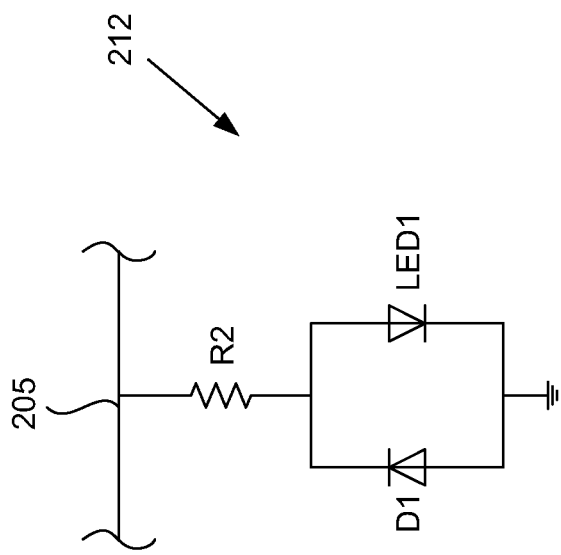
FIG. 8 shows a circuit diagram of an example circuit implementation of indication circuitry in the control unit.

FIG. 8 shows an example circuit implementation of indication circuitry 212 coupled to the output path 205. The indication circuitry 212 may include a light emitting diode LED1 that outputs a light signal or is "on" when RF energy is being supplied to the output 206. A resistor R2 controlling an amount of current supplied to LED1 may have a resistance of about 750Ω. In addition, the indication circuitry 212 may include a diode D1 connected anti-parallel to the LED1.

The indication circuitry 212 may identify to an operator when to cease application of the RF energy. For example, the operator may remove bias on a foot pedal or other RF actuator when the LED turns from "on" to "off."

Figure 9:
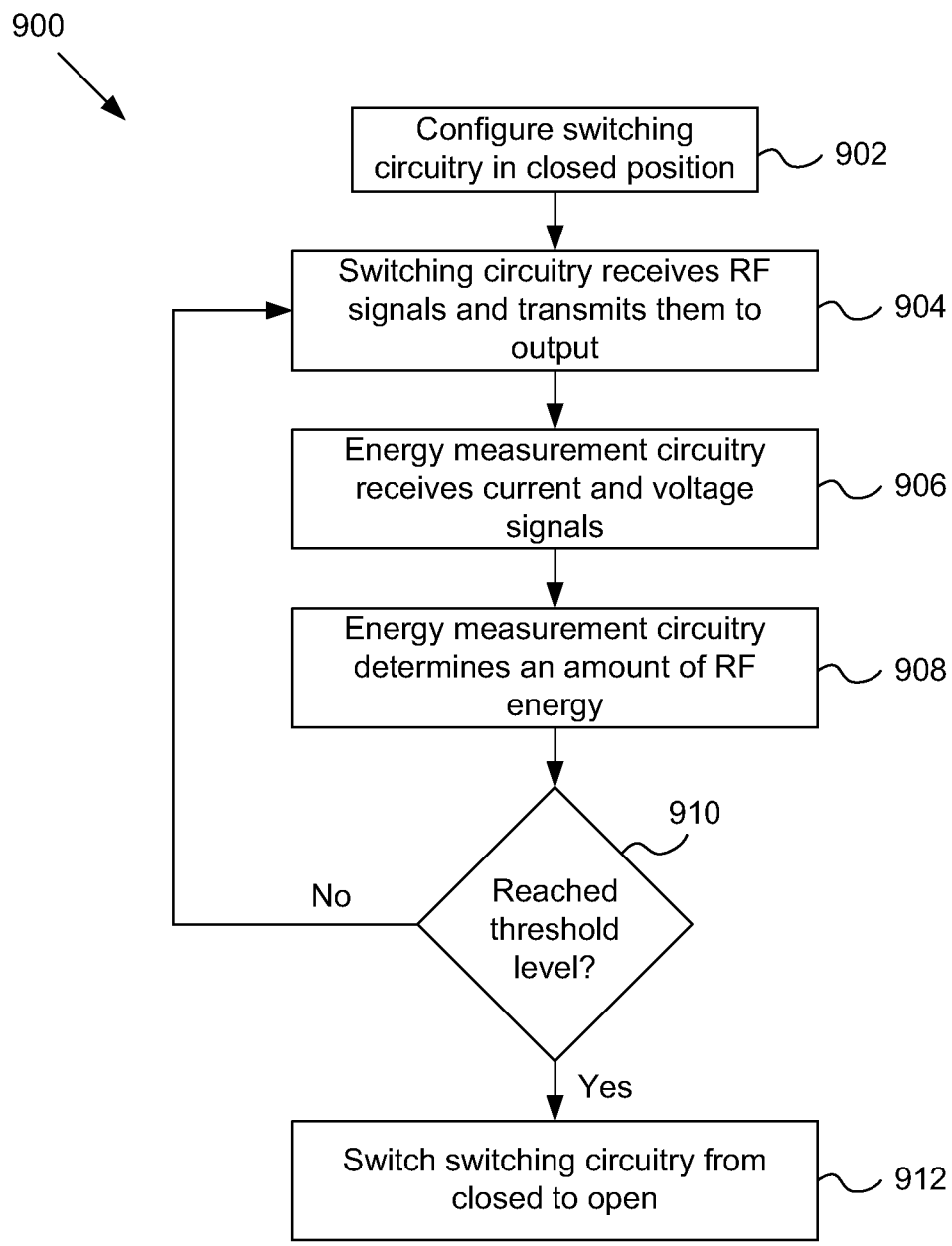
FIG. 9 shows a flow chart of an example method operating a control unit coupled to a RF generator to control transmission of RF energy to a medical device positioned at a treatment site within a patient.

FIG. 9 shows a flow chart of an example method 900 of operating a control unit coupled to a RF generator to control transmission of RF energy to a medical device positioned at a treatment site within a patient. At block 902, switching circuitry of the control unit, such as one or more relays, may be positioned or configured in a closed state. At block 904, the switching circuitry may receive the RF energy, and in the closed state, output the RF energy to an output of the control unit. At block 906, a portion of the RF energy output by the switching circuitry may be received by energy measurement circuitry of the control unit. The portion of the RF energy may be received as energy indicative or, representative of, and/or proportional to the voltage and current being supplied to the medical device.

At block 908, the energy measurement circuitry may determine an amount of RF energy, such as an amount of total energy, being output by the control unit and supplied to the medical device. At block 910, the energy measurement circuitry may determine whether the RF energy has reached a threshold level, which may be a predetermined or selected level that when exceeded (or substantially exceeded), may cause harm to the patient. If the energy measurement circuitry determines that the RF energy has not reached the threshold level, then the method may proceed back to block 904, where the switching circuitry may continue to receive RF energy from the RF generator and transmit the RF energy to the output of the control unit. Alternatively, if the energy measurement circuitry determines that the RF energy has reached the threshold level, then the method may proceed to block 912, where the energy measurement circuitry may cause the switching circuitry to switch from the closed state to an open state, such as by inducing current through an electromagnetic device of a relay in the switching circuitry.

Figure 10:
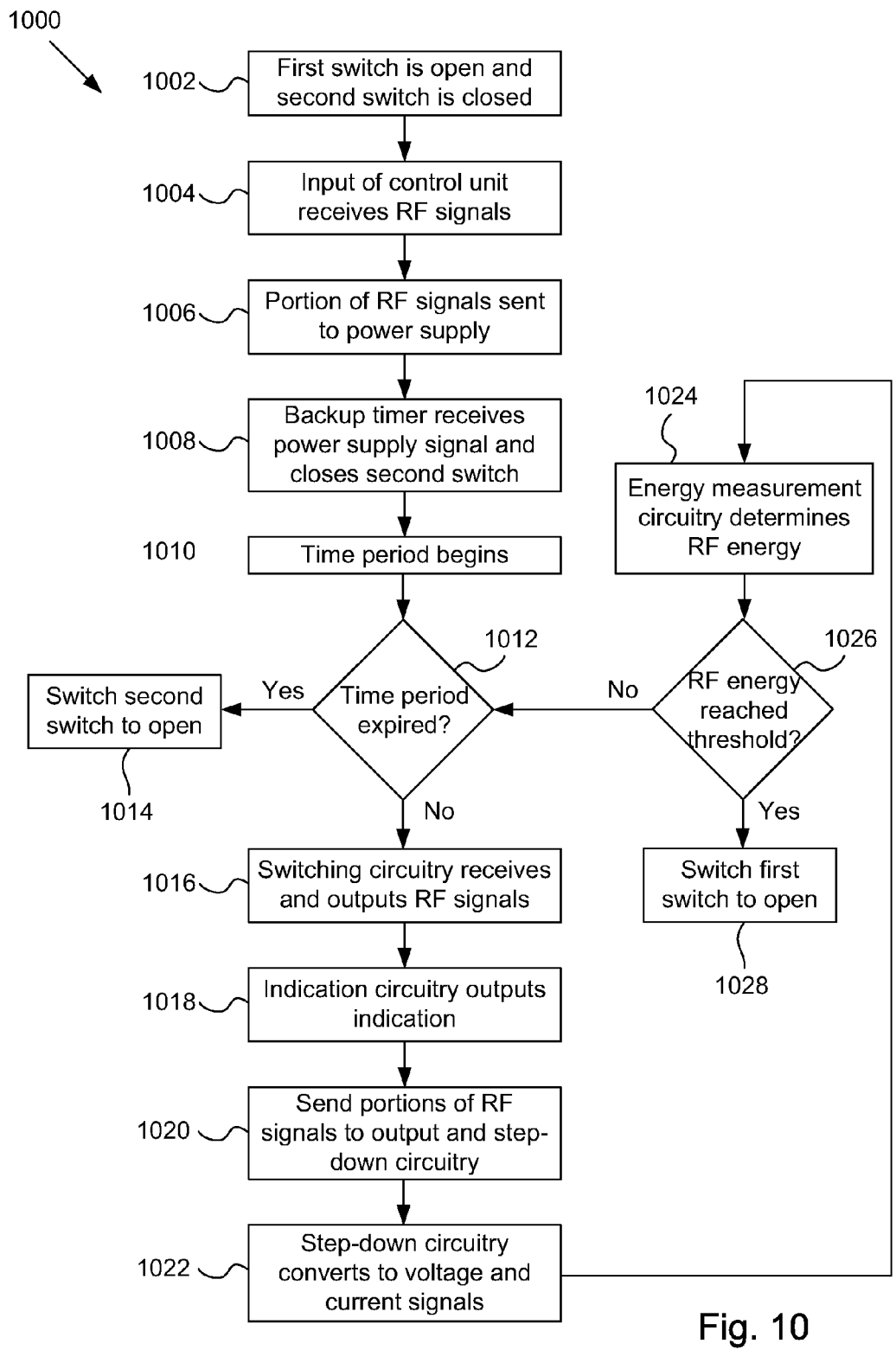
FIG. 10 shows a flow chart of an example method operating a control unit coupled to a RF generator to control transmission of RF energy to a medical device positioned at a treatment site within a patient.

FIG. 10 shows a flow chart of an alternative example method 1000 of operating a control unit coupled to a RF generator to control transmission of RF energy to a medical device positioned at a treatment site within a patient. At block 1002, a first switch of switching circuitry of the control unit may be configured in a closed state, and a second switch of the switching circuitry connected in series with the first switch may be configured in an open state. At block 1004, an input of the control unit may receive RF energy from the RF generator. At block 1006, a portion of the RF energy received by the input may be supplied to power supply circuitry of the control unit, which the power supply circuitry may use to generate one or more power supply energy.

At block 1008, backup timer circuitry of the control unit may receive a power supply signal from the power supply circuitry, and upon reception, may cause the second switch in the switching circuitry to switch from the open state to the closed state. At block 1010, a time period determined by a RC time constant in the backup timer may begin. At block 1012, the backup timer circuitry may determine if the time period has expired. If the time period as expired, then at block 1014, the backup timer may cause the second switch to switch to an open state, which may prevent RF energy output from the RF generator from being output by the control unit. Alternatively, if the timer period has not expired, then the method may proceed to block 1016.

At block 1016, a remaining portion of the RF energy that is not sent to the power supply circuitry may be sent to the switching circuitry because both the first switch and the second switch may now be configured in the closed state. Also, at block 1016, the switching circuitry may output the received RF energy along an output path to an output of the control unit. At block 1018, indication circuitry may receive a portion of the RF energy output by the switching circuitry, and in response, may output an indication, such as a light output, indicating to an operator that RF energy is being output by the control unit and supplied to the medical device. At block 1020, a portion of the RF energy that was not sent to the indication circuitry may be sent to step-down circuitry, and a remaining portion may be sent to an output of the control unit, where the remaining portion may be supplied to the medical device at a treatment site.

At block 1022, the portion sent to the step-down circuitry may be converted to signals proportional to the RF energy being supplied to the medical device. At block 1024, energy measurement circuitry may receive the signals from the step-down circuitry, and from the received signals, may determine an amount of RF energy, such as an amount of total energy, being output by the control unit and supplied to the medical device. At block 1026, the energy measurement circuitry may determine whether the RF energy has reached a threshold level. If the energy measurement circuitry determines that the RF energy has not reached the threshold level, then the method may proceed back to block 1012, where the switching circuitry may determine whether the time period has expired.

Alternatively, if the energy measurement circuitry determines that the RF energy has reached the threshold level, then the method may proceed to block 1028, where the energy measurement circuitry may cause the first switch of the switching circuitry to switch from the closed state to an open state, such as by inducing current through an electromagnetic device of a relay in the first switch, which may prevent RF energy from being output by the control unit to the medical device.

Figure 11:
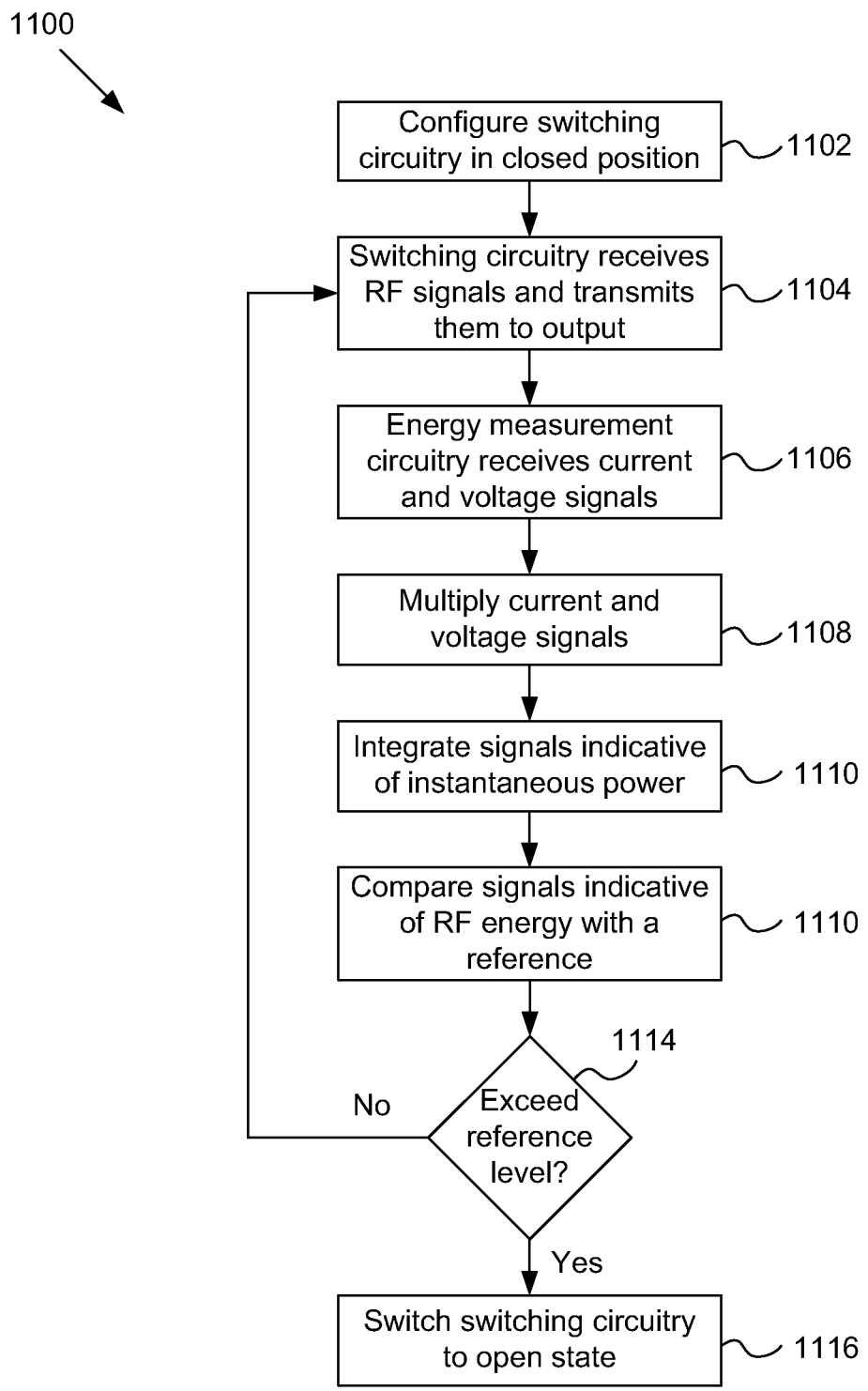
FIG. 11 shows a flow chart of an example method operating a control unit coupled to a RF generator to control transmission of RF energy to a medical device positioned at a treatment site within a patient.

FIG. 11 shows a flow chart of an alternative example method 1100 of operating a control unit coupled to a RF generator to control transmission of RF energy to a medical device positioned at a treatment site within a patient. At block 1102, switching circuitry may be configured in a closed state. At block 1104, the switching circuitry, in the closed state, may receive RF energy and transmit the received RF energy to an output of the control unit. At block 1106, a portion of the RF energy output from the switching circuitry may be sent to energy measurement circuitry as signals indicative of voltage and current being supplied to the medical device.

At block 1108, a multiplier of the energy measurement circuitry may multiply signals indicative of the voltage with signals indicative of the current, and generate a signal indicative of the instantaneous power being supplied to the medical device. At block 1110, an integrator of the energy measurement circuitry may integrate the signals indicative of the instantaneous power and generate signals indicative of the total energy being supplied to the medical device. At block 1112, a comparator of the energy measurement circuitry may compare the signals indicative of the or total energy with a reference value. At block 1114, the comparator may determine whether the signals indicative of the total energy have exceeded a reference level. If the reference level is not exceeded, then the method may proceed back to block 1104. Alternatively, if the reference level is not exceeded, then at block 1116, the comparator may output a signal that causes the switching circuitry to switch from the closed state to the open state, preventing RF energy from being output from the control unit to the medical device.

Figure 12:
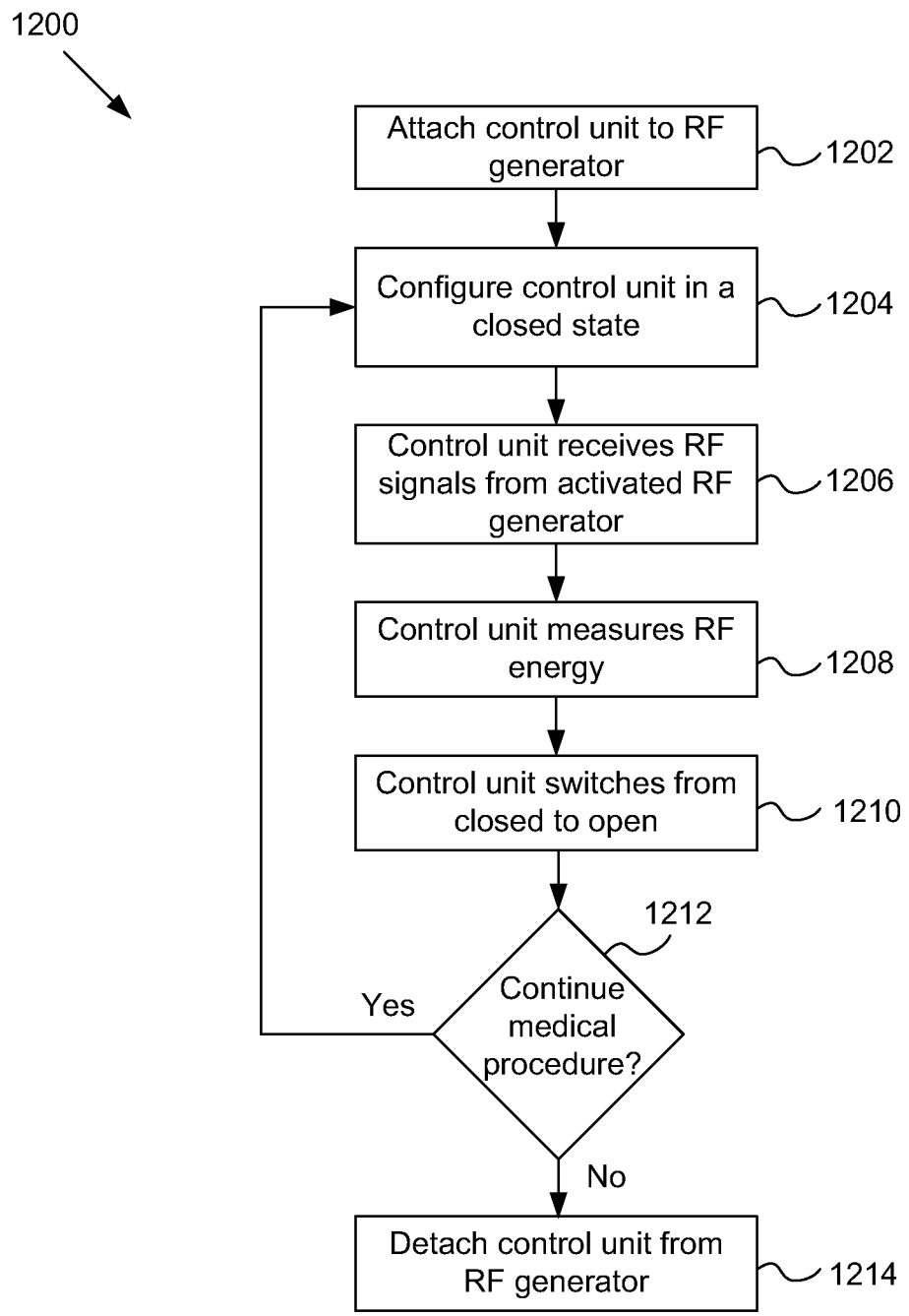
FIG. 12 shows a flow chart of an example method operating a control unit coupled to a RF generator to control transmission of RF energy to a medical device positioned at a treatment site within a patient.

FIG. 12 shows a flow chart of an alternative example method 1200 of operating a control unit in conjunction with a RF generator to control transmission of RF energy to a medical device positioned at a treatment site within a patient during a medical procedure. At block 1202, an input of the control unit may be coupled to an output of the RF generator. At block 1204, the control unit may be configured in a closed state. At block 1206, the RF generator may be activated and the control unit may receive RF energy from the RF generator and output the RF energy to a medical device at the treatment site. At block 1208, the control unit may measure the RF energy being supplied to the medical device. At block 1210, the control unit may switch from the closed state to the open state when the control unit detects that the RF energy being supplied to the medical device has reached a threshold level. At block 1212, if more RF energy is to be supplied to the treatment site, then the method may proceed back to block 1204, where the control unit may be configured in the closed state. Alternatively, if no more RF energy is to be supplied to the treatment site, then the method may proceed to block 1214, where the medical procedure has ended and the control unit may be detached from the RF generator.

Figure 13:
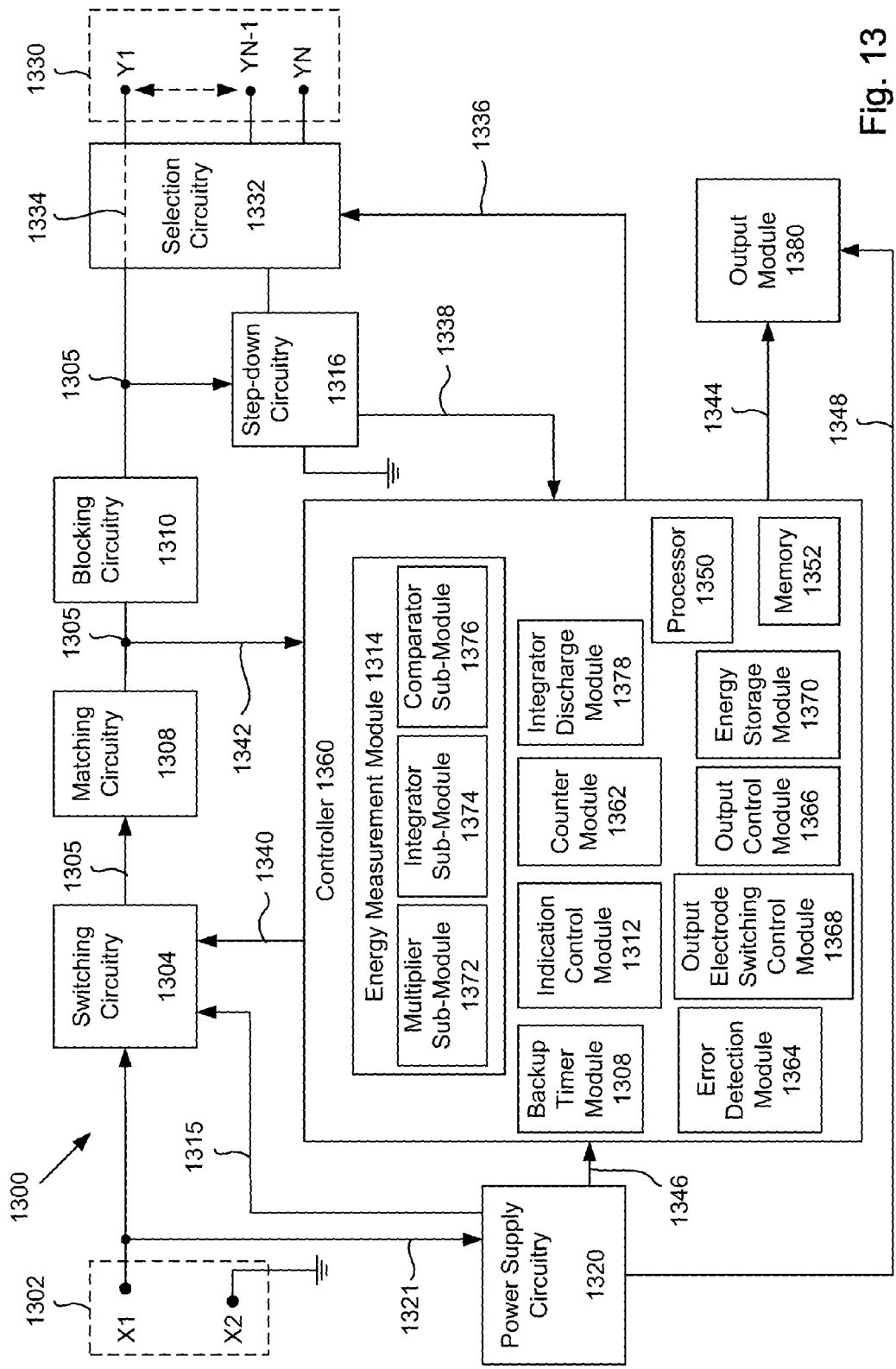
FIG. 13 shows a block diagram of another example control unit.

FIG. 13 shows another example control unit 1300 that may be used with the example medical system 100 instead of the example control unit 102. The control unit 1300 may include an input 1302 having a pair of input terminals X1, X2, switching circuitry 1304, matching circuitry 1308, blocking circuitry 1310, step-down circuitry 1316, each of which may have the same or similar configurations as the input 202, the switching circuitry 204, the matching circuitry 208, the blocking circuitry 210, and the step-down circuitry 216 for the control unit 102, as previously described.

The control unit 1300 may further include a controller 1360 that includes various modules to perform various functions of the control unit 1300. In particular, the controller 1360 may include an energy measurement module 1314, a backup timer module 1308, an indication control module 1312, a counter module 1362, an error indication control module 1364, an output control module 1366, an output electrode switching control module 1368, and an energy storage module 1370.

The energy measurement module 1314 may be configured to perform the same or similar functions as the energy measurement circuitry 214 of the control unit 102, including measuring an amount of energy that is being supplied to the medical device 106, determining when the amount of RF energy reaches a threshold level, and causing the switching circuitry 204 to switch between open and closed states to control whether RF energy may be sent to the medical device 106. The energy measurement module 1314 may include a multiplier sub-module 1372, an integrator sub-module 1374, and a comparator sub-module 1376. The multiplier, integrator, and comparator sub-modules 1372, 1374, and 1376 may be configured to perform the same functions, operate in the same way, and/or have any of the configurations of the multiplier circuitry 402, the integrator circuitry 404, and the comparator circuitry 406 shown and described with references to FIGS. 5 and/or 5A.

In addition, the backup timer module 1308 may be configured to perform the same or similar functions as the backup timer circuitry 218 and be implemented in the same or similar way as the backup timer circuit 218A or 218B as shown and described with references to FIGS. 6 and/or 6A.

The control unit 1300 may also include power supply circuitry 1320 that is configured to power various components of the control unit 1300, including the switching circuitry 1304 via connection 1315, the controller 1360 via connection 1346, and an output module 1380 via connection 1348. In addition, similar to the power supply circuitry 220 of the control unit 102, a portion of the RF energy received from the RF generator 104 may be sent to the power supply circuitry 1320 via a connection 1321, which may be used by the power supply circuitry 1320 to power the various components of the control unit 130.

Figure 17:
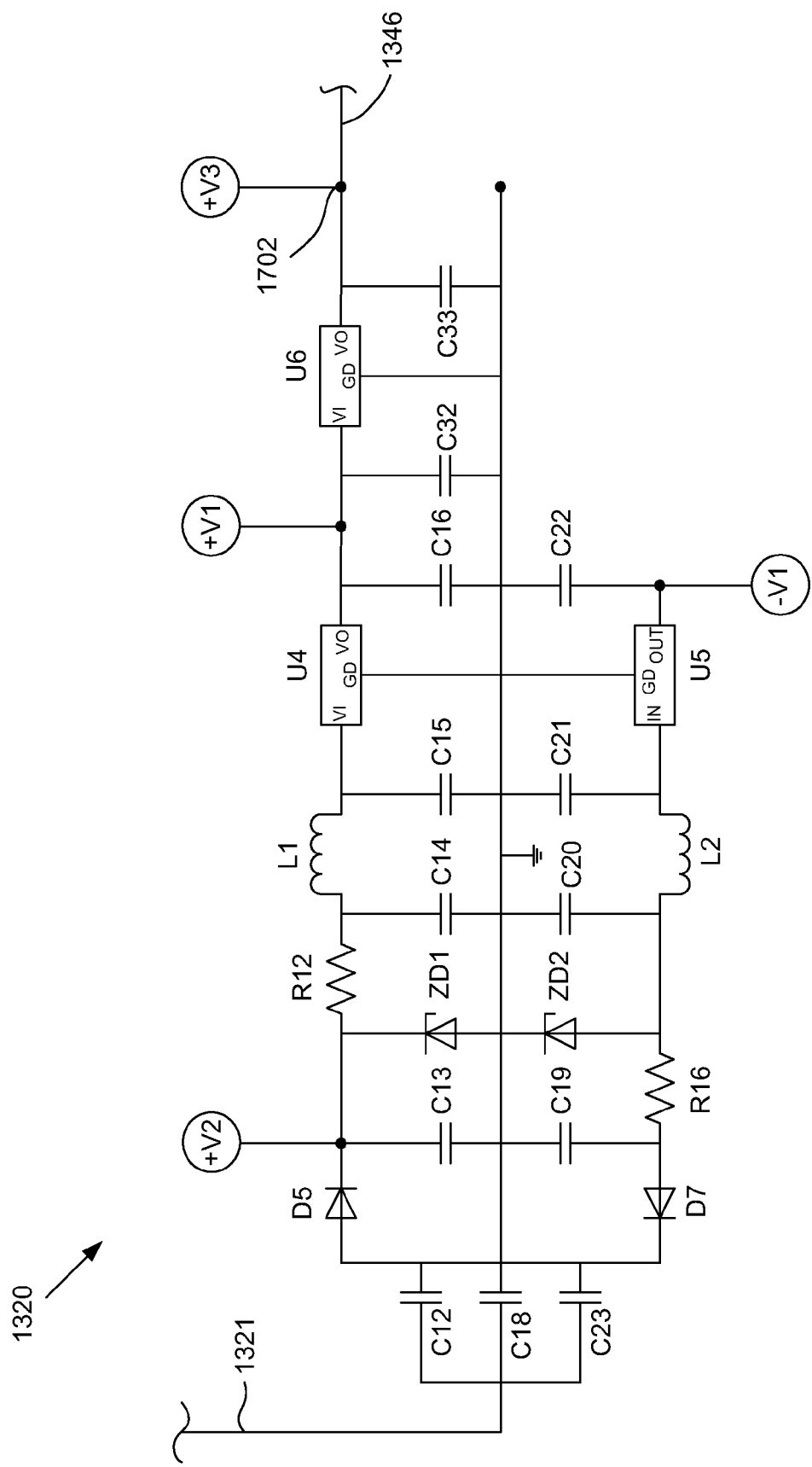
FIG. 17 shows a circuit diagram of an example circuit implementation of power supply circuitry for the control unit shown in FIG. 13.

FIG. 17 shows an example circuit implementation of the power supply circuitry 1320. The power supply circuitry 1320 may be configured to generate and output one or more positive power supply (e.g., DC power supply) signals and/or one or more negative power supply (e.g., DC power supply) signals. The example circuit implementation of the power supply circuitry 1320 may be similar to the example circuit implementation of the power supply circuitry 220 shown and described with reference to FIG. 7, except that the power supply circuitry 1320 may be configured to generate a third (additional) positive power supply +V3, which may be used to power the controller 1360 via connection 1346. To generate the third positive power supply +V3, the circuit elements including the resistor R5 and capacitors C26-C29 of the power supply circuitry 220 shown in FIG. 7 may be replaced with capacitors C32 and C33 and a voltage regulator U6, as shown in FIG. 17. The voltage regulator U6 may be configured to output the third positive power supply +V3 at node 1702, which may be connected to connection 1346 to power the controller 1360. An example voltage of the third positive power supply +V3 may be 3.3 volts, although other voltages may be used. For some example configurations, the other power supplies +V1, +V2, and −V1 may also be applied to one or more circuit components and/or modules of the controller 1360, as appropriate. An example capacitance for the capacitor C32 may be 0.1 μF and an example capacitance for the capacitor C33 may be 1 μF, although other capacitance values may be used.

Referring back to FIG. 13, the control unit 1300 may also include output 1330, which may include an N-number of output terminals Y1 to YN, where N is three or greater. The N-number of output terminals Y1 to YN may be configured to deliver RF energy to an N-number of electrodes of the medical device 106. The control unit 1300 may also include selection circuitry 1332, which may be configured to selectively or switchingly couple two of the N-number of output terminals Y1-YN to an output path 1305 while selectively isolating the other of the N-number of output terminals Y1-YN from the output path 1305 at any point in time. The two output terminals Y1-YN that are coupled to the input 1305 may be configured to deliver RF energy to respective electrodes of the medical device 106, provided that the switching circuitry 1304 is closed. In addition, the two output terminals Y1 to YN that are coupled to the output path 1305 may be coupled via the resistive network of the step-down circuitry 1316, which may be the same as or similar to the configuration of the terminals X3, X4 of the output 206, as shown in FIGS. 2 and 4. The two output terminals Y1 to YN that are coupled may provide to the energy measurement module 1314 scaled down signals that are proportional to the voltage and current being supplied to the medical device 106. The other output terminals Y1-YN that are not coupled to and/or that are isolated from the input 1302 may not deliver RF energy to respective electrodes of the medical device 106.

For some example configurations, the selection circuitry 1332, which may include one or more switches, may be configured to selectively couple any two of the N-number of output terminals Y1 to YN to the output path 1305. For alternative example configurations, one of the output terminals (e.g., output terminal Y1 shown in FIG. 13) may be a common output terminal that is always or fixedly coupled to the output path 1305, as shown by dotted line 1334, while the other of the N-number of output terminals Y1 to YN may be selectively coupled to the output path 1305 via the selection circuitry 1332. The selection circuitry 1332 may be configured to selectively couple the N-number of output terminals Y1 to YN by being configured in different states or configurations. For example, in one state, the selection circuitry 1332 may couple a first pair of output terminals Y1 to YN to the output path 1305, and in a different state, the selection circuitry 1332 may couple a second, different pair of output terminals Y1 to YN to the output path 1305. Two pairs of output terminals Y1 to YN may be different from each other when at least one of the output terminals Y1 to YN is not common between the two pairs.

In one example configuration, N may be three such that there are three output terminals Y1, Y2, and Y3 of the control unit 1302. One of the output terminals—e.g., output terminal Y1—may be fixedly coupled to the output path 1305, while the other output terminals Y2 and Y3 may be selectively coupled to the output path 1305 via the selection circuitry 1332. The selection circuitry 1332 may be configured in one of two different states. In a first state, the selection circuitry 1332 may electrically couple output terminal Y2 to the output path 1305, such that when RF energy is delivered through the control unit 1300 to the medical device 106, the RF energy is delivered through the output terminals Y1 and Y2, while the output terminal Y3 does not deliver RF energy to the medical device 106. In a second state, the selection circuitry 1332 may electrically couple output terminal Y3 to the output path 1305, such that when RF energy is delivered through the control unit 1300 to the medical device 106, the RF energy is delivered through output terminals Y1 and Y3, while the output terminal Y2 does not deliver RF energy to the medical device 106.

Selective coupling and/or the states or configurations in which the selection circuitry 1332 performs selective coupling between the output path 1305 and the N-number of output terminals Y1 to YN may be controlled by the output electrode switching control module 1368 of the controller 1360. The electrode switching control module 1368 may be configured to output control signals, such as switching signals, to the selection circuitry 1332 via a connection 1336 to configure the selection circuitry 1332 in a desired state or configuration.

For some examples, the desired state of the selection circuitry 1332 may depend on a predetermined treatment cycle or scheme, during which different pairs of electrodes may be alternatingly activated or supplied RF energy to perform an electrosurgical procedure on associated portions of an area of tissue at a treatment site. One example situation where different pairs of three or more electrodes may be alternatively activated in accordance with a treatment cycle or scheme may be where there is a low amount of output power generated by the RF generator 104 relative to a total area of tissue to undergo treatment by the electrosurgical procedure. For example, the output power generated by the RF generator 104 may be insufficient to ablate a total area of tissue using only a single supply or pulse of RF energy using two electrodes. If the output power of RF generator 104 used for the electrosurgical procedure cannot be increased, then the area of tissue undergoing treatment (e.g., being ablated) may be decreased. One way to do this may be to divide the area of tissue undergoing treatment into a plurality of portions. Rather than position and reposition a pair of electrodes over the plurality of portions, different pairs of electrodes may be positioned at the treatment site to contact the different portions of tissue. The different pairs of electrodes may then be alternatingly activated to treat the different portions of the tissue. The treatment cycle or scheme may identify or determine the way in which the different pairs of electrodes may be alternatively activated. The treatment cycle or scheme may be considered complete when all of the different pairs of electrodes have been alternatingly activated to treat all of the portions of the tissue area and/or a threshold amount of RF energy has been supplied to all of the different pairs of electrodes, as determined by comparator sub-module 1376 and/or the output electrode switching control module 1368. In other words, a treatment cycle or scheme may be complete when all of the different portions of the tissue area have been treated.

Figure 14:
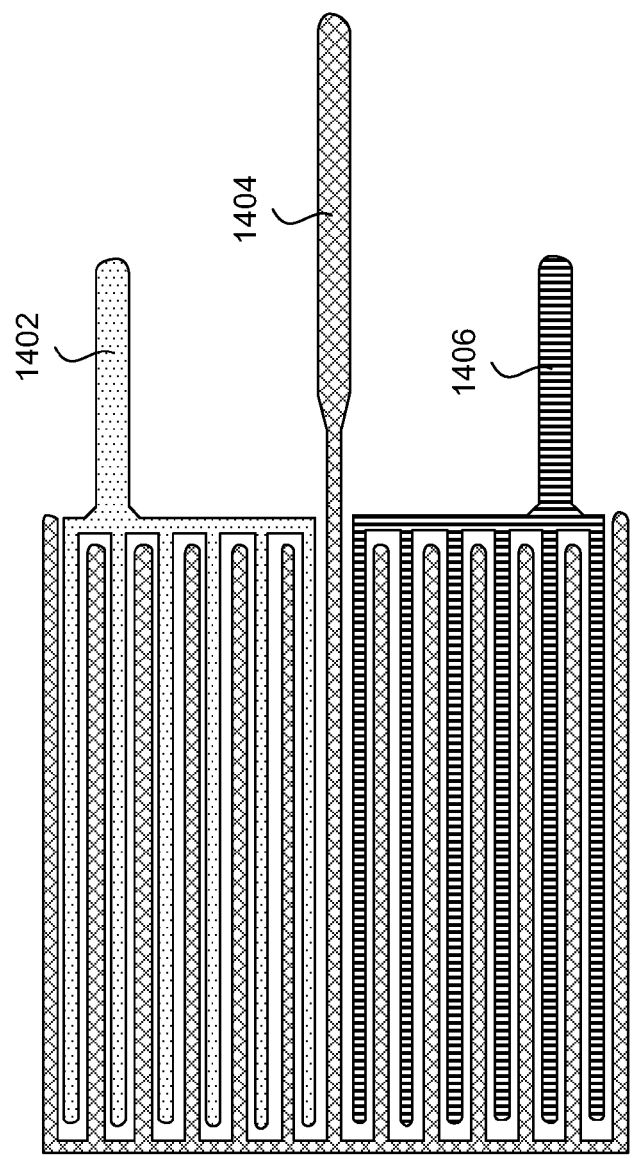
FIG. 14 shows a top view of an example electrode assembly having three electrodes.

As an illustration, three electrodes (i.e., N=3) may be configured into two different pairs of electrodes to ablate two different portions of an area of tissue to be ablated. FIG. 14 shows an example electrode assembly 1400 that includes three electrodes—a first electrode 1402, a second electrode 1404, and a third electrode 1406. The second electrode 1404 may be common to the first and third electrodes 1402, 1406. In the configuration of the electrode assembly 1400, the second electrode 1404 may be interdigitated with each of the first electrode 1402 and the third electrode 1406 such that the second, common electrode 1404 extends over an entire area of tissue to be ablated, while the first electrode 1402 is interdigitated with a portion of the second electrode 1404 such that their interdigitation is configured to extend over a first portion of the tissue area, and the third electrode 1406 is interdigitated with a portion of the second electrode 1404 such that their interdigitation extends over a second portion of the tissue area. During a first part of a treatment cycle or scheme associated with the electrode assembly 1400, RF energy may be supplied to the first and second electrodes 1402, 1404 to ablate the first portion of the tissue area. During a second part of the treatment cycle or scheme, RF energy may be supplied to the second and third electrodes 1404, 1406 to ablate a second portion of the tissue area. Similar configurations or implementations may be applied to alternative electrode assemblies having an N-number of electrodes greater than 3.

Referring back to FIG. 13, during operation of the control unit 1300, the switching circuitry 1304 may be closed to deliver RF energy to the medical device 106 (e.g., the electrode assembly 1400). Before RF energy is delivered, the output electrode switching control module 1368 may be configured to output a control signal to the selection circuitry 1332 via the connection 1336, which may configure the selection circuitry 1332 in a first state that electrically couples a first pair of the output terminals Y1 to YN to the output path 1305. RF energy may then be supplied to a pair of electrodes corresponding to the pair of output terminals Y1 to YN that are coupled to the output path 1305 to treat a first portion of tissue area during a first part of a treatment cycle or scheme. The energy measurement module 1314 may be configured to measure the RF energy being supplied to the medical device 106 from the step-down circuitry 1316 via connection 1338. The comparator sub-module 1376 may be configured to compare the RF energy being supplied to a threshold level. When the supplied RF energy reaches the threshold level, the comparator sub-module 1376 may be configured to output a control signal via connection 1340 to the switching circuitry 1304 to open the switching circuitry 1304.

After the supplied RF energy reaches the threshold level and the switching circuitry 1304 is opened, the output electrode switching control module 1368 may be configured to output another control signal to the selection circuitry 1332 via connection 1336, which may configure the selection circuitry 1332 in a second state that electrically couples a second pair of the output terminals Y1 to YN to the output path 1305. The switching circuitry 1304 may again be closed, and RF energy may then be supplied to a different pair of electrodes corresponding to the second pair of output terminals Y1 to YN that are coupled to the output path 1305 to treat a second portion of the tissue area during a second part of the treatment cycle or scheme. When the supplied energy reaches the threshold level, the comparator sub-module 1376 may be configured to output a control signal via connection 1340 to again open the switching circuitry 1304. The above operation may be repeated until all of the different pairs of electrodes have been activated to treat the different portions of the tissue area in accordance with a predetermined ablation cycle or scheme.

The controller 1360 may further include an integrator discharge module 1378 that is configured to discharge charge stored in the integrator sub-module 1374 in between supplies of pulses of RF energy delivered to the medical device during an electrosurgical procedure performed over the course of a treatment cycle or scheme. The integrator sub-module 1374, which may have the configuration of the integrator circuitry 404 as previously described with reference to FIG. 5, may include a diode D3 that provides a discharge path for charge stored across the capacitor C11 to discharge when the power supply circuitry 1320 is no longer supplying power. Conversely, when the power supply circuitry 1320 is supplying power, the diode D3 may not provide a discharge path for charge stored across the capacitor C11 to discharge. Like the control unit 102, the control unit 1300 may be a self-powering device or apparatus in that the power supply 1320 is configured to power various components of the control unit 1300 based on a portion of the RF energy received from the RF generator 104 via the input 1302 and connection 1321. As previously described, the RF generator 104 may generate RF output when an operator activates or engages an input device, such as a foot pedal. Accordingly, the integrator sub-module 1374 may not discharge charge stored across the capacitor C11 through the diode D3 as long as the input device of the RF generator 104 is being engaged by the operator.

To alternatingly supply an appropriate amount of RF energy to each of the different pairs of electrodes, such as in accordance with a treatment cycle or scheme, the charge stored in the capacitor C11 of the integrator sub-module 1374 may be discharged after each supply or pulse of RF energy to a selectively coupled pair of electrodes. One way to discharge the capacitor C11 is for the operator to disengage the input device after each pulse of RF energy so that the charge discharges through the diode D3. Alternatively, the integrator discharge module 1378 may be in communication with capacitor C11 and/or the output XINT of the integrator sub-module 1374 and be configured to selectively discharge charge stored across the capacitor C11 even if the input device of the RF energy is engaged 104 and the power supply circuitry 1320 is supplying power.

Figure 15:
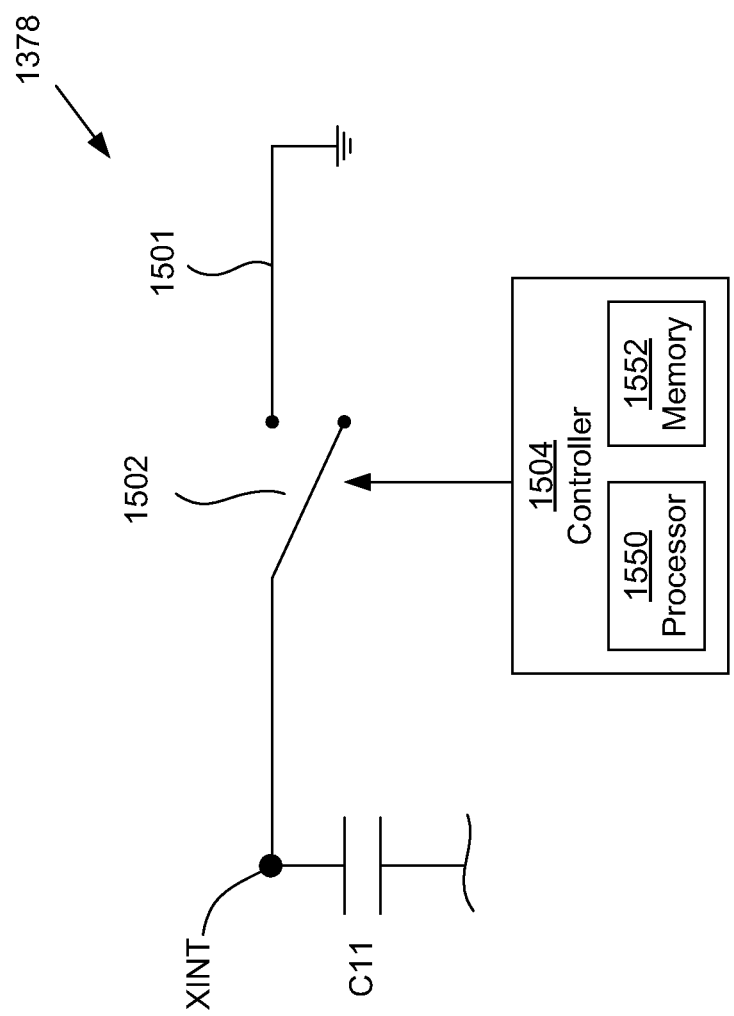
FIG. 15 shows a partial block and partial circuit schematic diagram of an example integrator discharge module.

FIG. 15 shows an example configuration of the integrator discharge module 1378 coupled to the capacitor C11 of the integrator sub-module 1374 via the output XINT. The integrator discharge module may include a discharge path 1501 connected to ground. The discharge module 1378 may also include a switch 1502 that alternatingly or selectively couples and decouples the discharge path 1501 to the capacitor C11 at the output XINT. When the switch 1502 is closed, the discharge path 1501 may be coupled to the capacitor C11 and charge stored in the capacitor C11 may be discharged through the discharge path 1501 to ground. Alternatively, when the switch 1502 is open, the discharge path 1501 may be decoupled from the capacitor C11 and charge stored in the capacitor C11 may not be or prevented from being discharged through the discharge path 1501.

The integrator discharge module 1378 may further include a controller 1504 that is configured to control switching of the switch 1502. The controller 1504 may include a processor 1550 that is configured to perform the functions of the controller 1504. The controller 1504 may also include a memory 1552 which may store computer executable instructions that may be accessed and/or executed by the processor 1550 to perform its functions.

The controller 1504 may be configured to determine whether to open or close the switch 1502 based on whether the switching circuitry 1304 is open or closed. For example, the controller 1504 may close the switch 1502 in response to a control signal sent by the comparator sub-module 1376 or the backup timer module 1308 when the supplied RF energy reaches a threshold level or when the time period expires. Either way, the controller 1504 may close the switch 1502 to discharge the capacitor C11 so that the integrator sub-module 1374 is reset and ready when the switching circuitry 1304 is closed (or re-closed) and a next supply or pulse of RF energy is supplied through the control unit 1300.

In addition or alternatively, the determination whether to open or close the switch 1502 may be based on the treatment cycle or scheme and where in the treatment cycle or scheme the ablation procedure is at. For example, after a pair of electrodes is activated and a portion of the tissue area is treated, the controller 1504 may determine whether another or next pair of electrodes are to be activated in accordance with the treatment cycle or scheme. If another or next pair of electrodes are to be activated, then the treatment cycle or scheme may not be complete, and the controller 1504 may be configured to close the switch 1502 to discharge the capacitor C11. Alternatively, if there is not another or next pair of electrodes to be activated, then the treatment cycle or scheme may be complete, and the controller 1504 may be configured to keep the switch 1502 open. In alternative configurations, control of the switch 1502 may not be based on the treatment cycle or scheme, and the switch 1502 may be closed after every time the switching circuitry 1304 is opened. In either case, the integrator sub-module 1374 may be reset for a next supply or pulse of RF energy, even if the input device of the RF generator 104 is kept engaged by the operator.

The controller 1360 may further include a counter module 1362 that may be configured to count and/or keep track of a number of times an electrosurgical procedure, such as an ablation procedure, is performed. The counter module 1362 may count the number of times an electrosurgical procedure is performed in various ways. For example, the counter module 1362 may count performance of the electrosurgical procedure and/or increase a count each time a supply or pulse of RF energy reaches a threshold level and the switching circuitry 1304 is opened. In addition or alternatively, the counter module 1362 may count performance of the electrosurgical procedure or increase a count each time a treatment cycle or scheme is completed. For example, where a treatment cycle includes alternatingly activating a first pair of electrodes and then a second pair of electrodes, the counter module 1362 may not count the electrosurgical procedure as being performed or increase the count until RF energy has been supplied to both the first and second pairs of electrodes.

The controller 1360 may further include an error detection module 1364 that is configured to detect or determine when a possible error or malfunction in performing an electrosurgical procedure has occurred. For example, if the backup timer module 1308 determines that the period of time has expired, the error detection module 1364 may determine that a possible error has occurred. In addition or alternatively, the error detection module 1364 may also detect or determine a possible error in response to the supplied RF energy reaching a threshold level too soon, which may indicate that the power settings on the RF generator 104 are set too high. The error detection module 1364 may also determine a type of an error output and/or content to include in an error output. Example types of outputs may include a visual output or an audio output. Example content may include information about the error, such as that the time period expired, improper or inadequate contact may have been made, or that the tissue was treated too quickly or too slowly as examples. Other types of outputs or content of the output may be possible.

The controller 1360 may further include an indication control module 1312 that may be configured to determine whether RF energy is being supplied or communicated through the output path 1305. The indication control module 1312 may detect whether RF energy is being supplied through the output path 1305 via connection 1342. As described in further detail below, an output module 1380 may be configured to output an indication of whether RF energy is being supplied through the output path 1305. The indication control module 1312 in combination with the output module 1380 may replace and/or be used instead of the indication circuitry 212 of the control unit 102.

The output module 1380 may be configured to generate and/or output one or more output signals or messages that indicates one or more of the determinations made by the controller 1360. For example, the output module 1380 may be configured to output a count of a number of electrosurgical procedures performed or a number of times RF energy is supplied to the medical device, as determined by the counter module 1362, an indication of whether RF energy is being supplied through the output path 1305 as determined by the ablation indication control module 1312, and an error indication as determined by the error detection module 1364. Other output signals or messages may be possible. The output signals or messages may be visual signals, audio signals, or combinations thereof. The output module 1380 may include one or more output devices, such as a display or other video output device, a light output device (e.g., a LED), an audio output device (e.g., a speaker) as examples, to generate and/or output the output signals or messages. An output control module 1366 of the controller 1360 may be configured to control the output module 1380 and/or communicate output signals to the output module 1380 via connection 1344. The output module 1380 may be powered by the power supply circuitry 1320 via connection 1346, such as to power on a display, an amplifier, or an LED as non-limiting examples.

For some example configurations, the controller 1360 may also include an energy storage module 1370 that may be configured to power one or more of the modules of the controller 1360 and/or the output module 1380, particularly when the power supply circuitry 1320 is not supplying power. When the power supply circuitry 1320 is activated and supplying power, at least some of the power being supplied may be stored as energy by the energy storage module 1370. When the power supply circuitry is deactivated, such as when the RF generator 104 is no longer supplying RF energy to the control unit 1300, the energy stored by the energy storage module 1370 may be used to power and/or keep activated the output module 1380 and/or all or some of the modules of the controller 1360 for a predetermined period of time. In this way, the output signals or messages being output by the output module 1380 may continue to be output by the output module 1380 for a predetermined period of time after the RF generator 104 is deactivated, such as when the operator of the RF generator 104 disengages the input device (e.g., the operator's foot is released from the input pedal).

The energy storage module 1370 may include one or more capacitors or other types of energy-storage devices. For some example configurations, the energy storage module 1370 may be connected to node 1702 of the power supply circuitry 1320 and/or in parallel with the capacitor C33. Example capacitance values for the energy storage module 1370 may be in a range of about 1 mF to 1 F, although other capacitance values may be used.

The modules and sub-modules of the controller 1360 may be implemented in hardware or a combination of hardware and software. In addition, unless described otherwise, the modules and sub-modules may be implemented using a processor 1350 and/or a memory 1352. For example, the functions of the modules of the controller 1360 may be performed by the processor 1350. In addition or alternatively, the modules may include data representing instructions that are stored in the memory 1352 and executable by the process. In addition or alternatively, the modules and sub-modules may include one or more executable modules, at least some of which may be embodied in a non-transitory computer readable storage medium as executable instructions. Accordingly, unless described otherwise, the modules and sub-modules may be defined to be hardware executable by the processor 1350, such as a computer readable storage medium that may include instructions executable by the processor 1350, a field programmable gate array (FPGA), and/or various devices, components, circuits, gates, circuit boards, and the like that are executable, directed, and/or controlled for performance by the processor 1350.

The processors 550, 650, 1350, and 1550 may each be a general processor, a digital signal processor, a controller, a microcontroller, an application specific integrated circuit, a field programmable gate array, an analog circuit, a digital circuit, combinations thereof, or other now known or later developed processors. The processors 550, 650, 1350, and 1550 may be configured together or separately, and together or separately, they may be a single device, a plurality of devices, or a combination of devices, such as associated with a network or distributed processing. Any of various processing strategies may be used, such as multi-processing, multi-tasking, parallel processing, remote processing, or the like. The processors 550, 650, 1350, 1550 may be responsive to and/or configured to execute instructions stored as part of software, hardware, integrated circuits, firmware, micro-code, or the like.

The memory 552, 652, 1352, 1552 may be non-transitory computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media, and the like. The memory 552, 652, 1352, 1552 may be configured together or separately and/or and may be a single device or a combination of devices. The memory 552, 652, 1352, 1552 may be adjacent to, part of, networked with and/or removable from the processor. Logic encoded in one or more non-transitory computer readable storage media for execution is defined as the instructions that are executable by the programmed processors 550, 650, 1350, 1550 and that are provided on the computer-readable storage media, memories, or a combination thereof.

The memory 552, 652, 1352, 1552 may be a computer readable storage media having stored therein data representing instructions executable by the programmed processors 550, 650, 1350, 1550. The memory 552, 652, 1352, 1552 may store instructions for the processors 550, 650, 1350, 1550. The processors 550, 650, 1350, 1550 may be programmed with and execute the instructions. The functions, acts, methods, or tasks illustrated in the figures or described herein may be performed by the programmed processors 550, 650, 1350, 1550 executing the instructions stored in the memory 552, 652, 1352, 1552. The functions, acts, methods or tasks may be independent of the particular type of instructions set, storage media, processor or processing strategy and may be performed by software, hardware, integrated circuits, firmware, micro-code, and the like, operating alone or in combination. The instructions may be for implementing the processes, techniques, methods, or acts described herein.

Figure 16:
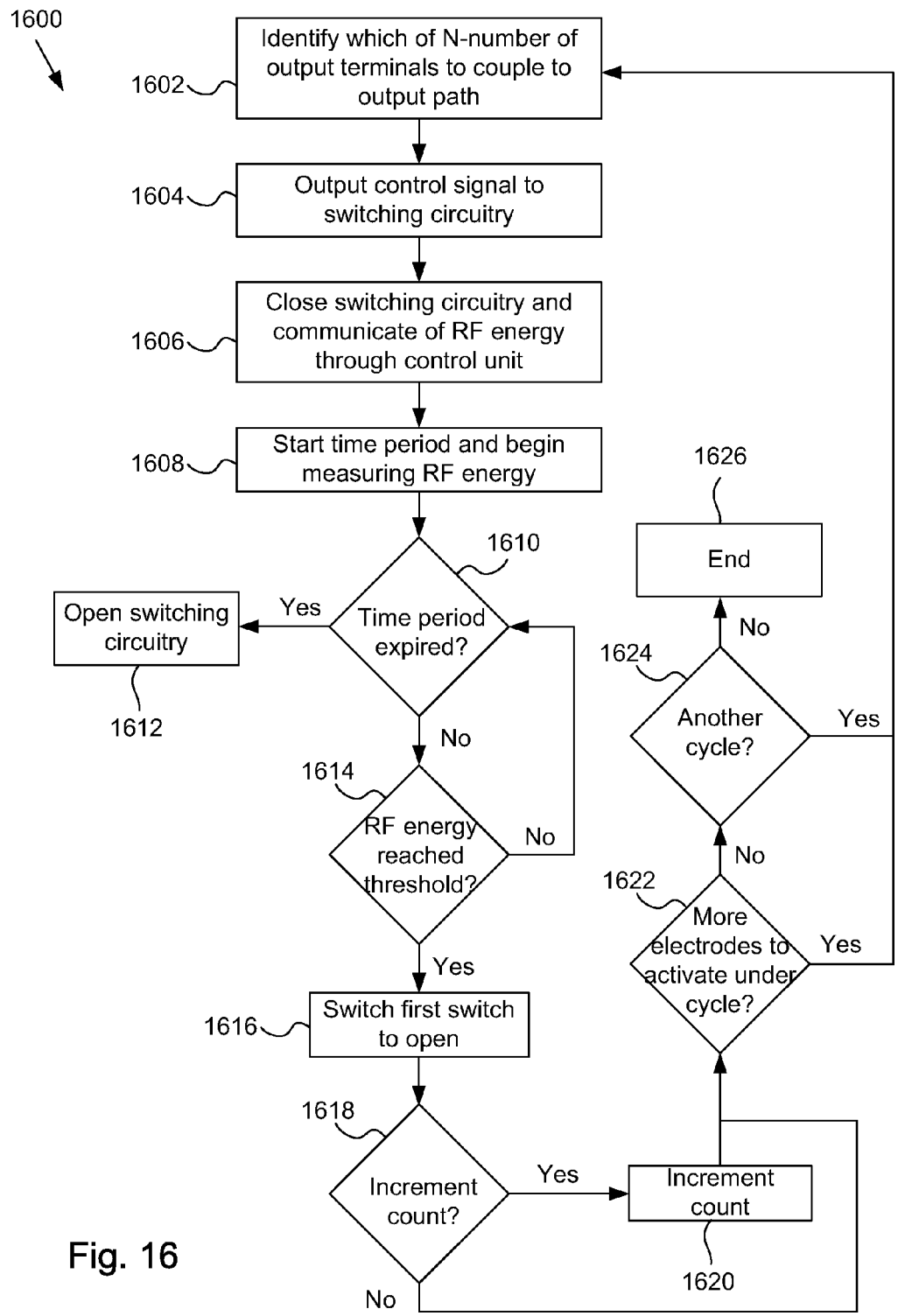
FIG. 16 shows a flow chart of another example method of operating a control unit coupled to a RF generator to control transmission of RF energy to a medical device positioned at a treatment site within a patient.

FIG. 16 shows a flow chart of another example method 1600 of operating a control unit coupled to a RF generator to control transmission of RF energy to a medical device positioned at a treatment site within a patient for performance of an electrosurgical procedure. At block 1602, a controller of the control unit may identify which of an N-number of output terminals to couple to an output path of the control unit, where N may be three or greater. Each output terminal may be electrically coupled to one of an N-number of electrodes of the medical device. The determination of which output terminals to couple may be based on a treatment cycle or scheme that may identify different pairs of the N-number of electrodes to be alternatively activated to treat different portions of a total area of tissue to be treated during performance of the electrosurgical procedure. The treatment cycle or scheme may also identify an order in which the different pairs of electrodes are to be activated.

At block 1604, the controller may output a control signal to selection circuitry. In response to the control signal, the selection circuitry may be configured to a desired state to selectively couple one more output terminals identified at block 1602 to the output path. At block 1606, switching circuitry of the control unit may be closed and RF energy may be received by and communicated through the control unit to the medical device. At block 1608, the controller may start a time period and the controller may begin calculating the RF energy being communicated through the control unit to the medical device. The start of the time period may indicate an initial time when RF energy is being applied to the electrodes.

At block 1610, the controller may determine if the time period has expired. If the time period has expired, then at block 1612, the controller may open the switching circuitry. Also, if the time period has expired, at block 1612, an output module of the control unit may output an error message indicative of the expiration of the time period. Alternatively, if the time period has not expired, then at block 1614, the controller may determine if the RF energy supplied to the electrodes has reached a threshold. The determination may be based on an energy measurement made by an energy measurement module of the controller, which may measure the RF energy as it is being supplied to the medical device. If the supplied RF energy has not reached the threshold, then the method 1600 may proceed back to block 1610, where the controller may determine if the time period has expired. Alternatively, if at block 1614 the supplied RF energy has reached the threshold, then at block 1616, the controller may open the switching circuitry.

At block 1618, the controller may determine whether to increment a count indicating a number of times an electrosurgical procedure and/or a number of times a supply or a pulse of RF energy is delivered to the medical device. The count may be displayed by the output module. The determination may be based on the RF energy reaching the threshold. Additionally, the determination may be based on whether the predetermined treatment cycle or scheme has ended. For example, if the treatment cycle or scheme is not complete and there are other pairs of electrodes to activate to complete the treatment cycle or scheme, then the controller may determine not to increment the count. Alternatively, if the treatment cycle or scheme is complete, then the controller may determine to increment the count. Alternatively, the controller may determine to increment the count when the switching circuitry is turned off in response to the supplied RF energy reaching the threshold level and without consideration of the cycle or scheme.

If the controller determines to increment the count, then at block 1620 the count may be incremented and the incremented count may be displayed by the output module. The method 1600 may then proceed to block 1622. Alternatively, if the controller determines not to increment the count, then the method 1600 may proceed directly to block 1622. At block 1622, the controller may determine whether other or next pairs of electrodes are to be activated under the treatment cycle or scheme. If there are, then the method 1600 may proceed back to block 1602, where the controller may identify which of the N-number of output terminals to couple to the output path. Alternatively, if there no more pairs of electrodes to activate under the treatment cycle or scheme, then at block 1624, the controller may determine if the N-number of electrodes are to be activated under a next or another treatment cycle or scheme. If so, then the method 1600 may proceed back to block 1602. If not, then the method 1600 may end at block 1626.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A control unit that is configured to control delivery of radio frequency (RF) energy to a medical device, the control unit comprising:
    switching circuitry configured to permit a first portion of the RF energy received from an RF generator to be output by the control unit to a medical device when configured in a closed state, and prevent the first portion of the RF energy from being output by the control unit to the medical device when configured in an open state;
    energy measurement circuitry configured to determine that an amount of the first portion of the RF energy delivered to the medical device has reached a threshold level, and switch the switching circuitry from the closed state to the open state upon a determination that an amount of the first portion of the RF energy has reached the threshold level;
    an output module configured to output at least one of: a first indication indicating a number of times an electrosurgical procedure is performed, a second indication indicating whether the first portion of the RF energy is being communicated through the control unit, or a third indication indicating an error associated with the electrosurgical procedure;
    power supply circuitry configured to, while the control unit is receiving the RF energy from the RF generator, convert a second portion of the RF energy to one or more power supplies, and supply a first portion of the one or more power supplies to the energy measurement circuitry and the output module; and
    an energy storage module configured to store a second portion of the one or more power supplies while the control unit is receiving RF energy from the RF generator, and when the control unit stops receiving the RF energy from the RF generator, power at least one of the output module or the energy measurement circuitry for a predetermined period of time using the stored second portion of the one or more power supplies.

2. The control unit of claim 1, further comprising:
    a plurality of output terminals adapted for electric coupling with the medical device; and
    selection circuitry configurable in a plurality of states, and when configured in each of the plurality of states, is configured to couple at least one and less than all of the plurality of output terminals to an output path of the control unit.

3. The control unit of claim 2, wherein the plurality of output terminals comprises three or more terminals, and when the selection circuitry is configured in each of the states, only two of the three or more output terminals are coupled to the output path.

4. The control unit of claim 2, further comprising a controller configured to configure the selection circuitry in the plurality of states according to a treatment scheme that identifies an order in which at least two of the plurality of output terminals are alternatingly coupled to the output path.

5. The control unit of claim 2, wherein one of the plurality of output terminals is fixedly coupled to the output path and the selection circuitry is configured to alternatingly couple the other of the plurality of output terminals to the output path.

6. The control unit of claim 2, further comprising:
a controller configured to change a current state of the selection circuitry so that a different pair of the plurality of output terminals is coupled to the output path in response to the determination by the energy measurement circuitry that the amount of RF energy supplied to the medical device has reached the threshold level.

7. The control unit of claim 2, further comprising a controller configured to count the number of times the electrosurgical procedure is performed.

8. The control unit of claim 7, wherein the controller is configured to increment the number when the amount of the first portion of the RF energy is determined to have reached the threshold level.

9. The control unit of claim 8, wherein the controller is configured to increment the number further when all different pairs of the plurality of output terminals have been alternatingly coupled to the output path and have delivered the threshold level of RF energy to the medical device.

10. The control unit of claim 1, wherein the energy measurement circuitry comprises integrator circuitry configured to perform an integration indicative of an amount of RF energy delivered to the medical device, and wherein the control unit further comprises:
an integrator discharge module configured to discharge a capacitor of the integrator circuitry when the amount of first portion of the RF energy is determined to have reached the threshold level.

11. A method of controlling delivery of radio frequency (RF) energy from a RF generator to a medical device with a control unit coupled to the RF generator and the medical device, the method comprising:
configuring switching circuitry of the control unit in a closed state;
receiving, at an input of the control unit, the RF energy from the RF generator;
transmitting, with the switching circuitry in the closed state, a first portion of the RF energy along an output path to a plurality of output terminals of the control unit;
sending a second portion of the RF energy from the input to power supply circuitry;
while the input of the control unit is receiving the RF energy from the RF generator:
converting, with the power supply circuitry, the second portion of the RF energy to one or more power supplies;
powering energy measurement circuitry of the control unit with a first portion of the one or more power supplies; and
storing, with an energy storage module, a second portion of the one or more power supplies; and
when the control unit stops receiving the RF energy from the RF generator, powering an output module for a pre-determined period of time with the stored second portion of the one or more power supplies from the energy storage module.

12. The method of claim 11, further comprising:
configuring selection circuitry in one of a plurality of states, wherein the selection circuitry, when configured in each of the plurality of states, couples at least one and less than all of the plurality of output terminals to the output path of the control unit; and
outputting the first portion of the RF energy from the control unit to the medical device via the at least one and less than all of the plurality of output terminals being coupled to the output path by the selection circuitry.

13. The method of claim 12, wherein the plurality of output terminals comprises three or more terminals, and when the selection circuitry is configured in each of the states, only two of the three or more output terminals are coupled to the output path.

14. The method of claim 12 further comprising outputting, with a controller of the control unit, a control signal to the selection circuitry to configure the selection circuitry in the plurality of states according to a treatment scheme that identifies an order in which at least two of the plurality of output terminals are alternatingly coupled to the output path.

15. The method of claim 12, further comprising:
alternatingly coupling, with the selection circuitry, at least two of the plurality of output terminals to the output path, while one of the plurality of output terminals is fixedly coupled to the output path.

16. The method of claim 12, wherein the control signal comprises a first control signal, the method further comprising:
determining, with comparator circuitry of the control unit, when an amount of the first portion of the RF energy supplied to the medical device via a pair of the plurality of output terminals reaches a threshold level; and
in response to determining that the RF energy has reached the threshold level, outputting, with the controller, a second control signal to change a current state of the selection circuitry so that a different pair of the plurality of output terminals is coupled to the output path.

17. The method of claim 12, further comprising:
counting, with a controller, a number of times an electrosurgical procedure is performed with the medical device.

18. The method of claim 17, wherein counting the number of times comprises incrementing, with the controller, a count in response to a determination that an amount of the first portion of the RF energy delivered to the medical device has reached a threshold level.

19. The method of claim 18, wherein incrementing the number comprises incrementing, with the controller, the count when all different pairs of the plurality of output terminals have been alternatingly coupled to the output path and have delivered the threshold level of RF energy to the medical device.

20. The method of claim 11, further comprising:
while the output module is being powered for the predetermined time period with the stored second portion of the one or more power supplies, outputting, with the output module, at least one of: a first indication indicating a number of times an electrosurgical procedure is performed or a second indication indicating an error associated with the electrosurgical procedure.

* * * * *